US010716665B2

(12) United States Patent
Quill et al.

(10) Patent No.: US 10,716,665 B2
(45) **Date of Patent: *Jul. 21, 2020**

(54) TRANSCATHETER VALVE WITH TORSION SPRING FIXATION AND RELATED SYSTEMS AND METHODS

(71) Applicant: MEDTRONIC, INC., Minneapolis, MN (US)

(72) Inventors: Jason Quill, Forest Lake, MN (US); Cynthia T. Clague, Minnetonka, MN (US); Paul T. Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 216 days.

This patent is subject to a terminal disclaimer.

(21) Appl. No.: 15/903,642

(22) Filed: Feb. 23, 2018

(65) Prior Publication Data

US 2018/0185142 A1 Jul. 5, 2018

Related U.S. Application Data

(63) Continuation of application No. 14/156,076, filed on Jan. 15, 2014, now Pat. No. 9,925,044, which is a (Continued)

(51) Int. Cl.
*A61F 2/24* (2006.01)

(52) U.S. Cl.
CPC .......... *A61F 2/2418* (2013.01); *A61F 2/2436* (2013.01); *A61F 2220/0008* (2013.01); (Continued)

(58) Field of Classification Search
CPC .......... A61F 2002/821; A61F 2002/828; A61F 2/2403; A61F 2/2418; A61F 2/243; (Continued)

(56) References Cited

U.S. PATENT DOCUMENTS

| | | |
|---|---|---|
| 3,334,629 A | 8/1967 | Cohn |
| 3,409,013 A | 11/1968 | Berry |

(Continued)

FOREIGN PATENT DOCUMENTS

| | | |
|---|---|---|
| CN | 101011298 A | 8/2007 |
| DE | 3640745 C2 | 3/1992 |

(Continued)

OTHER PUBLICATIONS

Andersen, H. et al., "Transluminal implantation of artificial heart valves. Description of a new expandable aortic valve and initial results with implantation by catheter technique in closed chest pigs." *Euro. Heart J.* 13:704-708 (1992).

(Continued)

*Primary Examiner* — Sarah W Aleman
(74) *Attorney, Agent, or Firm* — Medler Ferro Woodhouse & Mills PLLC

(57) ABSTRACT

Described is a prosthetic valve, comprising: an expandable stent including an inner lumen and having a first and a second end; and a spring attached to the first end of the expandable stent; wherein the expandable stent and the spring can expand radially to a desired diametric configuration in order to anchor the prosthetic valve at an implantation position in a body lumen. Related systems and methods.

20 Claims, 14 Drawing Sheets

Related U.S. Application Data continuation of application No. 12/846,962, filed on Jul. 30, 2010, now Pat. No. 8,652,204.

(60) Provisional application No. 61/320,111, filed on Apr. 1, 2010.

(52) U.S. Cl.
CPC ................. *A61F 2220/0016* (2013.01); *A61F 2230/0013* (2013.01)

(58) Field of Classification Search
CPC ...... A61F 2/2436; A61F 2/2439; A61F 2/848; A61F 2/86; A61F 2/88; A61F 2/95
See application file for complete search history.

(56) References Cited

U.S. PATENT DOCUMENTS

| | | | |
|---|---|---|---|
| 3,540,431 | A | 11/1970 | Mobin-Uddin |
| 3,587,115 | A | 6/1971 | Shiley |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Edwards et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 4,035,849 | A | 7/1977 | Angell et al. |
| 4,056,854 | A | 11/1977 | Boretos et al. |
| 4,078,268 | A | 3/1978 | Possis |
| 4,106,129 | A | 8/1978 | Carpentier et al. |
| 4,222,126 | A | 9/1980 | Boretos et al. |
| 4,233,690 | A | 11/1980 | Akins |
| 4,265,694 | A | 5/1981 | Boretos et al. |
| 4,291,420 | A | 9/1981 | Reul |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,425,908 | A | 1/1984 | Simon |
| 4,470,157 | A | 9/1984 | Love |
| 4,491,986 | A | 1/1985 | Gabbay |
| 4,501,030 | A | 2/1985 | Lane |
| 4,574,803 | A | 3/1986 | Storz |
| 4,580,568 | A | 4/1986 | Gianturco |
| 4,592,340 | A | 6/1986 | Boyles |
| 4,610,688 | A | 9/1986 | Silvestrini et al. |
| 4,612,011 | A | 9/1986 | Kautzky |
| 4,647,283 | A | 3/1987 | Carpentier et al. |
| 4,648,881 | A | 3/1987 | Carpentier et al. |
| 4,655,771 | A | 4/1987 | Wallsten |
| 4,662,885 | A | 5/1987 | DiPisa, Jr. |
| 4,665,906 | A | 5/1987 | Jervis |
| 4,681,908 | A | 7/1987 | Broderick et al. |
| 4,710,192 | A | 12/1987 | Liotta et al. |
| 4,733,665 | A | 3/1988 | Palmaz |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,819,751 | A | 4/1989 | Shimada et al. |
| 4,834,755 | A | 5/1989 | Silvestrini et al. |
| 4,846,830 | A | 7/1989 | Knoch et al. |
| 4,856,516 | A | 8/1989 | Hillstead |
| 4,872,874 | A | 10/1989 | Taheri |
| 4,878,495 | A | 11/1989 | Grayzel |
| 4,878,906 | A | 11/1989 | Lindemann et al. |
| 4,883,458 | A | 11/1989 | Shiber |
| 4,909,252 | A | 3/1990 | Goldberger |
| 4,917,102 | A | 4/1990 | Miller et al. |
| 4,922,905 | A | 5/1990 | Strecker |
| 4,954,126 | A | 9/1990 | Wallsten |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 5,002,559 | A | 3/1991 | Tower |
| 5,007,896 | A | 4/1991 | Shiber |
| 5,026,366 | A | 6/1991 | Leckrone |
| 5,032,128 | A | 7/1991 | Alonso |
| 5,037,434 | A | 8/1991 | Lane |
| 5,047,041 | A | 9/1991 | Samuels |
| 5,059,177 | A | 10/1991 | Towne et al. |
| 5,061,273 | A | 10/1991 | Yock |
| 5,085,635 | A | 2/1992 | Cragg |
| 5,089,015 | A | 2/1992 | Ross |
| 5,104,399 | A | 4/1992 | Lazarus |
| 5,108,425 | A | 4/1992 | Hwang |
| 5,152,771 | A | 10/1992 | Sabbaghian et al. |
| 5,161,547 | A | 11/1992 | Tower |
| 5,163,953 | A | 11/1992 | Vince |
| 5,167,628 | A | 12/1992 | Boyles |
| 5,178,632 | A | 1/1993 | Hanson |
| 5,217,483 | A | 6/1993 | Tower |
| 5,232,445 | A | 8/1993 | Bonzel |
| 5,272,909 | A | 12/1993 | Nguyen et al. |
| 5,295,958 | A | 3/1994 | Shturman |
| 5,327,774 | A | 7/1994 | Nguyen et al. |
| 5,332,402 | A | 7/1994 | Teitelbaum |
| 5,344,442 | A | 9/1994 | Deac |
| 5,350,398 | A | 9/1994 | Pavcnik et al. |
| 5,354,330 | A | 10/1994 | Hanson et al. |
| 5,370,685 | A | 12/1994 | Stevens |
| 5,389,106 | A | 2/1995 | Tower |
| 5,397,351 | A | 3/1995 | Pavcnik et al. |
| 5,397,355 | A | 3/1995 | Marin et al. |
| 5,411,552 | A | 5/1995 | Andersen et al. |
| 5,415,633 | A | 5/1995 | Lazarus et al. |
| 5,431,676 | A | 7/1995 | Dubrul et al. |
| 5,443,446 | A | 8/1995 | Shturman |
| 5,449,384 | A | 9/1995 | Johnson |
| 5,480,424 | A | 1/1996 | Cox |
| 5,489,294 | A | 2/1996 | McVenes et al. |
| 5,489,297 | A | 2/1996 | Duran |
| 5,496,346 | A | 3/1996 | Horzewski et al. |
| 5,500,014 | A | 3/1996 | Quijano et al. |
| 5,507,767 | A | 4/1996 | Maeda et al. |
| 5,545,209 | A | 8/1996 | Roberts et al. |
| 5,545,211 | A | 8/1996 | An et al. |
| 5,545,214 | A | 8/1996 | Stevens |
| 5,549,665 | A | 8/1996 | Vesely et al. |
| 5,554,185 | A | 9/1996 | Block et al. |
| 5,575,818 | A | 11/1996 | Pinchuk |
| 5,580,922 | A | 12/1996 | Park et al. |
| 5,591,195 | A | 1/1997 | Taheri et al. |
| 5,609,626 | A | 3/1997 | Quijano et al. |
| 5,645,559 | A | 7/1997 | Hachtman et al. |
| 5,665,115 | A | 9/1997 | Cragg |
| 5,667,523 | A | 9/1997 | Bynon et al. |
| 5,674,277 | A | 10/1997 | Freitag |
| 5,695,498 | A | 12/1997 | Tower |
| 5,702,368 | A | 12/1997 | Stevens et al. |
| 5,713,953 | A | 2/1998 | Vallana et al. |
| 5,716,417 | A | 2/1998 | Girard et al. |
| 5,720,776 | A | 2/1998 | Chuter et al. |
| 5,746,709 | A | 5/1998 | Rom et al. |
| 5,749,890 | A | 5/1998 | Shaknovich |
| 5,766,151 | A | 6/1998 | Valley et al. |
| 5,782,809 | A | 7/1998 | Umeno et al. |
| 5,800,456 | A | 9/1998 | Maeda et al. |
| 5,800,508 | A | 9/1998 | Goicoechea et al. |
| 5,817,126 | A | 10/1998 | Imran |
| 5,824,041 | A | 10/1998 | Lenker et al. |
| 5,824,043 | A | 10/1998 | Cottone, Jr. |
| 5,824,053 | A | 10/1998 | Khosravi et al. |
| 5,824,056 | A | 10/1998 | Rosenberg |
| 5,824,061 | A | 10/1998 | Quijano et al. |
| 5,824,064 | A | 10/1998 | Taheri |
| 5,840,081 | A | 11/1998 | Andersen et al. |
| 5,843,158 | A | 12/1998 | Lenker et al. |
| 5,851,232 | A | 12/1998 | Lois |

(56) References Cited

U.S. PATENT DOCUMENTS

| | | | |
|---|---|---|---|
| 5,855,597 | A | 1/1999 | Jayaraman |
| 5,855,601 | A | 1/1999 | Bessler et al. |
| 5,860,966 | A | 1/1999 | Tower |
| 5,861,028 | A | 1/1999 | Angell |
| 5,868,783 | A | 2/1999 | Tower |
| 5,876,448 | A | 3/1999 | Thompson et al. |
| 5,888,201 | A | 3/1999 | Stinson et al. |
| 5,891,191 | A | 4/1999 | Stinson |
| 5,906,619 | A | 5/1999 | Olson et al. |
| 5,907,893 | A | 6/1999 | Zadno-Azizi et al. |
| 5,908,451 | A | 6/1999 | Yeo |
| 5,908,452 | A | 6/1999 | Bokros et al. |
| 5,913,842 | A | 6/1999 | Boyd et al. |
| 5,925,063 | A | 7/1999 | Khosravi |
| 5,944,738 | A | 8/1999 | Amplatz et al. |
| 5,954,766 | A | 9/1999 | Zadno-Azizi et al. |
| 5,957,949 | A | 9/1999 | Leonhardt et al. |
| 5,964,405 | A | 10/1999 | Benary et al. |
| 5,968,068 | A | 10/1999 | Dehdashtian et al. |
| 5,984,957 | A | 11/1999 | Laptewicz, Jr. et al. |
| 5,997,573 | A | 12/1999 | Quijano et al. |
| 6,022,370 | A | 2/2000 | Tower |
| 6,027,525 | A | 2/2000 | Suh et al. |
| 6,029,671 | A | 2/2000 | Stevens et al. |
| 6,042,589 | A | 3/2000 | Marianne |
| 6,042,598 | A | 3/2000 | Tsugita et al. |
| 6,042,607 | A | 3/2000 | Williamson, IV et al. |
| 6,051,014 | A | 4/2000 | Jang |
| 6,059,809 | A | 5/2000 | Amor et al. |
| 6,076,742 | A | 6/2000 | Benary |
| 6,091,042 | A | 7/2000 | Benary |
| 6,102,944 | A | 8/2000 | Huynh et al. |
| 6,110,201 | A | 8/2000 | Quijano et al. |
| 6,113,612 | A | 9/2000 | Swanson et al. |
| 6,146,366 | A | 11/2000 | Schachar |
| 6,159,239 | A | 12/2000 | Greenhalgh |
| 6,162,208 | A | 12/2000 | Hipps |
| 6,162,245 | A | 12/2000 | Jayaraman |
| 6,168,614 | B1 | 1/2001 | Andersen et al. |
| 6,171,335 | B1 | 1/2001 | Wheatley et al. |
| 6,200,336 | B1 | 3/2001 | Pavcnik et al. |
| 6,203,550 | B1 | 3/2001 | Olson |
| 6,210,408 | B1 | 4/2001 | Chandrasekaran et al. |
| 6,218,662 | B1 | 4/2001 | Tchakarov et al. |
| 6,221,006 | B1 | 4/2001 | Dubrul et al. |
| 6,221,091 | B1 | 4/2001 | Khosravi |
| 6,241,757 | B1 | 6/2001 | An et al. |
| 6,245,102 | B1 | 6/2001 | Jayaraman |
| 6,248,116 | B1 | 6/2001 | Chevillon et al. |
| 6,258,114 | B1 | 7/2001 | Konya et al. |
| 6,258,115 | B1 | 7/2001 | Dubrul |
| 6,258,120 | B1 | 7/2001 | McKenzie et al. |
| 6,277,555 | B1 | 8/2001 | Duran et al. |
| 6,287,339 | B1 | 9/2001 | Vazquez et al. |
| 6,296,662 | B1 | 10/2001 | Caffey |
| 6,299,637 | B1 * | 10/2001 | Shaolian ............... A61F 2/2418 623/1.24 |
| 6,302,906 | B1 | 10/2001 | Goicoechea et al. |
| 6,309,382 | B1 | 10/2001 | Garrison et al. |
| 6,309,417 | B1 | 10/2001 | Spence et al. |
| 6,312,465 | B1 | 11/2001 | Griffin et al. |
| 6,327,772 | B1 | 12/2001 | Zadno-Azizi et al. |
| 6,338,735 | B1 | 1/2002 | Stevens |
| 6,348,063 | B1 | 2/2002 | Yassour et al. |
| 6,350,277 | B1 | 2/2002 | Kocur |
| 6,352,708 | B1 | 3/2002 | Duran et al. |
| 6,371,970 | B1 | 4/2002 | Khosravi et al. |
| 6,371,983 | B1 | 4/2002 | Lane |
| 6,379,383 | B1 | 4/2002 | Palmaz et al. |
| 6,380,457 | B1 | 4/2002 | Yurek et al. |
| 6,398,807 | B1 | 6/2002 | Chouinard et al. |
| 6,409,750 | B1 | 6/2002 | Hyodoh et al. |
| 6,425,916 | B1 | 7/2002 | Garrison et al. |
| 6,440,164 | B1 | 8/2002 | DiMatteo et al. |
| 6,454,799 | B1 | 9/2002 | Schreck |
| 6,458,153 | B1 | 10/2002 | Bailey et al. |
| 6,461,382 | B1 | 10/2002 | Cao |
| 6,468,303 | B1 | 10/2002 | Amplatz et al. |
| 6,475,239 | B1 | 11/2002 | Campbell et al. |
| 6,482,228 | B1 | 11/2002 | Norred |
| 6,488,704 | B1 | 12/2002 | Connelly et al. |
| 6,494,909 | B2 | 12/2002 | Greenhalgh |
| 6,503,272 | B2 | 1/2003 | Duerig et al. |
| 6,508,833 | B2 | 1/2003 | Pavcnik et al. |
| 6,527,800 | B1 | 3/2003 | McGuckin, Jr. et al. |
| 6,530,949 | B2 | 3/2003 | Konya et al. |
| 6,530,952 | B2 | 3/2003 | Vesely |
| 6,558,418 | B2 | 5/2003 | Carpentier et al. |
| 6,562,031 | B2 | 5/2003 | Chandrasekaran et al. |
| 6,562,058 | B2 | 5/2003 | Seguin et al. |
| 6,569,196 | B1 | 5/2003 | Vesely |
| 6,572,652 | B2 | 6/2003 | Shaknovich |
| 6,582,462 | B1 | 6/2003 | Andersen et al. |
| 6,585,758 | B1 | 7/2003 | Chouinard et al. |
| 6,592,546 | B1 | 7/2003 | Barbut et al. |
| 6,600,803 | B2 | 7/2003 | Bruder |
| 6,605,112 | B1 | 8/2003 | Moll et al. |
| 6,613,077 | B2 | 9/2003 | Gilligan et al. |
| 6,622,604 | B1 | 9/2003 | Chouinard et al. |
| 6,632,243 | B1 | 10/2003 | Zadno-Azizi et al. |
| 6,635,068 | B1 | 10/2003 | Dubrul et al. |
| 6,635,085 | B1 | 10/2003 | Caffey et al. |
| 6,652,571 | B1 | 11/2003 | White et al. |
| 6,652,578 | B2 | 11/2003 | Bailey et al. |
| 6,656,213 | B2 | 12/2003 | Solem |
| 6,663,663 | B2 | 12/2003 | Kim et al. |
| 6,669,724 | B2 | 12/2003 | Park et al. |
| 6,673,089 | B1 | 1/2004 | Yassour et al. |
| 6,673,109 | B2 | 1/2004 | Cox |
| 6,676,698 | B2 | 1/2004 | McGuckin, Jr. et al. |
| 6,682,558 | B2 | 1/2004 | Tu et al. |
| 6,682,559 | B2 | 1/2004 | Myers et al. |
| 6,685,739 | B2 | 2/2004 | DiMatteo et al. |
| 6,689,144 | B2 | 2/2004 | Gerberding |
| 6,689,164 | B1 | 2/2004 | Seguin |
| 6,692,512 | B2 | 2/2004 | Jang |
| 6,692,513 | B2 | 2/2004 | Streeter et al. |
| 6,695,878 | B2 | 2/2004 | McGuckin, Jr. et al. |
| 6,702,851 | B1 | 3/2004 | Chinn et al. |
| 6,719,789 | B2 | 4/2004 | Cox |
| 6,730,118 | B2 | 5/2004 | Spenser et al. |
| 6,730,121 | B2 | 5/2004 | Ortiz et al. |
| 6,730,377 | B2 | 5/2004 | Wang |
| 6,733,525 | B2 | 5/2004 | Yang et al. |
| 6,736,846 | B2 | 5/2004 | Cox |
| 6,752,828 | B2 | 6/2004 | Thornton |
| 6,758,855 | B2 | 7/2004 | Fulton, III et al. |
| 6,767,362 | B2 | 7/2004 | Schreck |
| 6,769,434 | B2 | 8/2004 | Liddicoat et al. |
| 6,786,925 | B1 | 9/2004 | Schoon et al. |
| 6,790,229 | B1 | 9/2004 | Berreklouw |
| 6,790,230 | B2 | 9/2004 | Beyersdorf et al. |
| 6,792,979 | B2 | 9/2004 | Konya et al. |
| 6,797,002 | B2 | 9/2004 | Spence et al. |
| 6,821,297 | B2 | 11/2004 | Snyders |
| 6,830,575 | B2 | 12/2004 | Stenzel et al. |
| 6,830,584 | B1 | 12/2004 | Seguin |
| 6,830,585 | B1 | 12/2004 | Artof et al. |
| 6,846,325 | B2 | 1/2005 | Liddicoat |
| 6,866,650 | B2 | 3/2005 | Stevens et al. |
| 6,872,223 | B2 | 3/2005 | Roberts et al. |
| 6,875,231 | B2 | 4/2005 | Anduiza et al. |
| 6,883,522 | B2 | 4/2005 | Spence et al. |
| 6,887,266 | B2 | 5/2005 | Williams et al. |
| 6,890,330 | B2 | 5/2005 | Streeter et al. |
| 6,893,460 | B2 | 5/2005 | Spenser et al. |
| 6,896,690 | B1 | 5/2005 | Lambrecht et al. |
| 6,908,481 | B2 | 6/2005 | Cribier |
| 6,913,600 | B2 | 7/2005 | Valley et al. |
| 6,929,653 | B2 | 8/2005 | Strecter |
| 6,936,066 | B2 | 8/2005 | Palmaz et al. |
| 6,939,365 | B1 | 9/2005 | Fogarty et al. |
| 6,951,571 | B1 | 10/2005 | Srivastava |
| 6,974,474 | B2 | 12/2005 | Pavcnik et al. |

(56) References Cited

U.S. PATENT DOCUMENTS 6,974,476 B2 12/2005 McGuckin, Jr. et al.
6,986,742 B2 1/2006 Hart et al.
6,989,027 B2 1/2006 Allen et al.
6,989,028 B2 1/2006 Lashinski et al.
6,991,649 B2 1/2006 Sievers
7,018,401 B1 3/2006 Hyodoh et al.
7,018,406 B2 3/2006 Seguin et al.
7,018,408 B2 3/2006 Bailey et al.
7,041,128 B2 5/2006 McGuckin, Jr. et al.
7,044,966 B2 5/2006 Svanidze et al.
7,048,014 B2 5/2006 Hyodoh et al.
7,097,659 B2 8/2006 Woolfson et al.
7,101,396 B2 9/2006 Artof et al.
7,105,016 B2 9/2006 Shiu et al.
7,115,141 B2 10/2006 Menz et al.
7,128,759 B2 10/2006 Osborne et al.
7,137,184 B2 11/2006 Schreck
7,147,663 B1 12/2006 Berg et al.
7,153,324 B2 12/2006 Case et al.
7,160,319 B2 1/2007 Chouinard et al.
7,175,656 B2 2/2007 Khairkhahan
7,186,265 B2 3/2007 Sharkawy et al.
7,195,641 B2 3/2007 Palmaz et al.
7,198,646 B2 4/2007 Figulla et al.
7,201,761 B2 4/2007 Woolfson et al.
7,201,772 B2 4/2007 Schwammenthal et al.
7,252,682 B2 8/2007 Seguin
7,261,732 B2 8/2007 Justino
7,267,686 B2 9/2007 DiMatteo et al.
7,300,457 B2 11/2007 Palmaz
7,300,463 B2 11/2007 Liddicoat
7,311,730 B2 12/2007 Gabbay
7,316,706 B2 1/2008 Bloom et al.
7,329,278 B2 2/2008 Seguin et al.
7,335,218 B2 2/2008 Wilson et al.
7,338,520 B2 3/2008 Bailey et al.
7,374,571 B2 5/2008 Pease et al.
7,377,938 B2 5/2008 Sarac et al.
7,381,218 B2 6/2008 Schreck
7,384,411 B1 6/2008 Condado
7,399,315 B2 7/2008 Iobbi
7,429,269 B2 9/2008 Schwammenthal et al.
7,442,204 B2 10/2008 Schwammenthal et al.
7,445,631 B2 11/2008 Salahieh et al.
7,462,191 B2 12/2008 Spenser et al.
7,470,284 B2 12/2008 Lambrecht et al.
7,470,285 B2 12/2008 Nugent et al.
7,481,838 B2 1/2009 Carpentier et al.
7,491,228 B2 2/2009 Doran et al.
7,524,331 B2 4/2009 Birdsall
7,544,206 B2 6/2009 Cohn
7,547,322 B2 6/2009 Sarac et al.
7,556,386 B2 7/2009 Smith
7,556,646 B2 7/2009 Yang et al.
7,585,321 B2 9/2009 Cribier
7,611,534 B2 11/2009 Kapadia et al.
7,611,535 B2 11/2009 Woolfson et al.
7,618,446 B2 11/2009 Andersen et al.
7,621,948 B2 11/2009 Hermann et al.
7,625,403 B2 12/2009 Krivoruchko
7,635,386 B1 12/2009 Gammie
7,637,946 B2 12/2009 Solem et al.
7,682,390 B2 3/2010 Seguin
7,748,389 B2 7/2010 Salahieh et al.
7,780,726 B2 8/2010 Seguin
7,806,919 B2 10/2010 Bloom et al.
7,955,377 B2 * 6/2011 Melsheimer .......... A61F 2/2418 623/1.24
7,959,672 B2 6/2011 Salahieh et al.
8,449,599 B2 5/2013 Chau et al.
9,060,892 B2 6/2015 Oepen et al.
2001/0001314 A1 5/2001 Davison et al.
2001/0002445 A1 5/2001 Vesely
2001/0007956 A1 7/2001 Letac et al.
2001/0010017 A1 7/2001 Letac et al.
2001/0011189 A1 8/2001 Drasler et al.
2001/0021872 A1 9/2001 Bailey et al.
2001/0025196 A1 9/2001 Chinn et al.
2001/0032013 A1 10/2001 Marton
2001/0039450 A1 11/2001 Pavcnik et al.
2001/0041928 A1 11/2001 Pavcnik et al.
2001/0044647 A1 11/2001 Pinchuk et al.
2002/0010508 A1 1/2002 Chobotov
2002/0026233 A1 2/2002 Shaknovich
2002/0029014 A1 3/2002 Jayaraman
2002/0032480 A1 3/2002 Spence et al.
2002/0032481 A1 3/2002 Gabbay
2002/0035396 A1 3/2002 Heath
2002/0042650 A1 4/2002 Vardi et al.
2002/0052651 A1 5/2002 Myers et al.
2002/0058995 A1 5/2002 Stevens
2002/0072789 A1 6/2002 Hackett et al.
2002/0077696 A1 6/2002 Zadno-Azizi et al.
2002/0095209 A1 7/2002 Zadno-Azizi et al.
2002/0099439 A1 7/2002 Schwartz et al.
2002/0103533 A1 8/2002 Langberg et al.
2002/0107565 A1 8/2002 Greenhalgh
2002/0111674 A1 8/2002 Chouinard et al.
2002/0123802 A1 9/2002 Snyders
2002/0133183 A1 9/2002 Lentz et al.
2002/0138138 A1 9/2002 Yang
2002/0151970 A1 10/2002 Garrison et al.
2002/0161392 A1 10/2002 Dubrul
2002/0161394 A1 10/2002 Macoviak et al.
2002/0186558 A1 12/2002 Plank et al.
2002/0193871 A1 12/2002 Beyersdorf et al.
2003/0014104 A1 1/2003 Cribier
2003/0023300 A1 1/2003 Bailey et al.
2003/0023303 A1 1/2003 Palmaz et al.
2003/0028247 A1 2/2003 Cali
2003/0036791 A1 2/2003 Philipp et al.
2003/0040771 A1 2/2003 Hyodoh et al.
2003/0040772 A1 2/2003 Hyodoh et al.
2003/0040792 A1 2/2003 Gabbay
2003/0050694 A1 3/2003 Yang et al.
2003/0055495 A1 3/2003 Pease et al.
2003/0065386 A1 4/2003 Weadock
2003/0069492 A1 4/2003 Abrams et al.
2003/0109924 A1 6/2003 Cribier
2003/0125795 A1 7/2003 Pavcnik et al.
2003/0130726 A1 7/2003 Thorpe et al.
2003/0130727 A1 7/2003 Drasler et al.
2003/0130729 A1 7/2003 Paniagua et al.
2003/0139804 A1 7/2003 Hankh et al.
2003/0149475 A1 8/2003 Hyodoh et al.
2003/0149476 A1 8/2003 Damm et al.
2003/0149478 A1 8/2003 Figulla et al.
2003/0153974 A1 8/2003 Spenser et al.
2003/0158595 A1 8/2003 Randall et al.
2003/0171805 A1 9/2003 Berg et al.
2003/0181850 A1 9/2003 Diamond et al.
2003/0191519 A1 10/2003 Lombardi et al.
2003/0195609 A1 10/2003 Berenstein et al.
2003/0199913 A1 10/2003 Dubrul et al.
2003/0199963 A1 10/2003 Tower et al.
2003/0199971 A1 10/2003 Tower et al.
2003/0199972 A1 10/2003 Zadno-Azizi et al.
2003/0209835 A1 11/2003 Chun et al.
2003/0212410 A1 11/2003 Stenzel et al.
2003/0212452 A1 11/2003 Zadno-Azizi et al.
2003/0212454 A1 11/2003 Scott et al.
2003/0225445 A1 12/2003 Derus et al.
2003/0236568 A1 12/2003 Hojeibane et al.
2004/0019374 A1 1/2004 Hojeibane et al.
2004/0034411 A1 2/2004 Quijano et al.
2004/0039436 A1 2/2004 Spenser et al.
2004/0044402 A1 3/2004 Jung et al.
2004/0049224 A1 3/2004 Buehlmann et al.
2004/0049262 A1 3/2004 Obermiller et al.
2004/0049266 A1 3/2004 Anduiza et al.
2004/0059429 A1 3/2004 Amin et al.
2004/0082904 A1 4/2004 Houde et al.
2004/0088045 A1 5/2004 Cox
2004/0092858 A1 5/2004 Wilson et al.

(56) References Cited

U.S. PATENT DOCUMENTS

| | | | |
|---|---|---|---|
| 2004/0092989 | A1 | 5/2004 | Wilson et al. |
| 2004/0093005 | A1 | 5/2004 | Durcan |
| 2004/0093060 | A1 | 5/2004 | Seguin et al. |
| 2004/0093070 | A1 | 5/2004 | Hojeibane et al. |
| 2004/0093075 | A1 | 5/2004 | Kuehne |
| 2004/0097788 | A1 | 5/2004 | Mourlas et al. |
| 2004/0098112 | A1 | 5/2004 | DiMatteo et al. |
| 2004/0106976 | A1 | 6/2004 | Bailey et al. |
| 2004/0106990 | A1 | 6/2004 | Spence et al. |
| 2004/0111096 | A1 | 6/2004 | Tu et al. |
| 2004/0116951 | A1 | 6/2004 | Rosengart |
| 2004/0117004 | A1 | 6/2004 | Osborne et al. |
| 2004/0122468 | A1 | 6/2004 | Yodfat et al. |
| 2004/0122514 | A1 | 6/2004 | Fogarty et al. |
| 2004/0122516 | A1 | 6/2004 | Fogarty et al. |
| 2004/0127979 | A1 | 7/2004 | Wilson et al. |
| 2004/0138742 | A1 | 7/2004 | Myers et al. |
| 2004/0138743 | A1 | 7/2004 | Myers et al. |
| 2004/0153146 | A1 | 8/2004 | Lashinski et al. |
| 2004/0167573 | A1 | 8/2004 | Williamson, IV et al. |
| 2004/0167620 | A1 | 8/2004 | Ortiz et al. |
| 2004/0186563 | A1 | 9/2004 | Lobbi |
| 2004/0193261 | A1 | 9/2004 | Berreklouw |
| 2004/0210240 | A1 | 10/2004 | Saint |
| 2004/0210304 | A1 | 10/2004 | Seguin et al. |
| 2004/0210307 | A1 | 10/2004 | Khairkhahan |
| 2004/0215333 | A1 | 10/2004 | Duran et al. |
| 2004/0215339 | A1 | 10/2004 | Drasler et al. |
| 2004/0225353 | A1 | 11/2004 | McGuckin, Jr. et al. |
| 2004/0225354 | A1 | 11/2004 | Allen et al. |
| 2004/0236411 | A1 | 11/2004 | Sarac et al. |
| 2004/0254636 | A1 | 12/2004 | Flagle et al. |
| 2004/0260389 | A1 | 12/2004 | Case et al. |
| 2004/0260394 | A1 | 12/2004 | Donk et al. |
| 2004/0267357 | A1 | 12/2004 | Allen et al. |
| 2005/0010246 | A1 | 1/2005 | Streeter et al. |
| 2005/0010285 | A1 | 1/2005 | Lambrecht et al. |
| 2005/0010287 | A1 | 1/2005 | Macoviak et al. |
| 2005/0015112 | A1 | 1/2005 | Cohn et al. |
| 2005/0027348 | A1 | 2/2005 | Case et al. |
| 2005/0033398 | A1 | 2/2005 | Seguin |
| 2005/0043790 | A1 | 2/2005 | Seguin |
| 2005/0049692 | A1 | 3/2005 | Numamoto et al. |
| 2005/0049696 | A1 | 3/2005 | Siess et al. |
| 2005/0055088 | A1 | 3/2005 | Liddicoat et al. |
| 2005/0060029 | A1 | 3/2005 | Le et al. |
| 2005/0060030 | A1 | 3/2005 | Lashinski et al. |
| 2005/0075584 | A1 | 4/2005 | Cali |
| 2005/0075712 | A1 | 4/2005 | Biancucci et al. |
| 2005/0075717 | A1 | 4/2005 | Nguyen et al. |
| 2005/0075719 | A1 | 4/2005 | Bergheim |
| 2005/0075720 | A1 | 4/2005 | Nguyen et al. |
| 2005/0075724 | A1 | 4/2005 | Svanidze et al. |
| 2005/0075725 | A1 | 4/2005 | Rowe |
| 2005/0075727 | A1 | 4/2005 | Wheatley |
| 2005/0075730 | A1 | 4/2005 | Myers et al. |
| 2005/0075731 | A1 | 4/2005 | Artof et al. |
| 2005/0085841 | A1 | 4/2005 | Eversull et al. |
| 2005/0085842 | A1 | 4/2005 | Eversull et al. |
| 2005/0085843 | A1 | 4/2005 | Opolski et al. |
| 2005/0085890 | A1 | 4/2005 | Rasmussen et al. |
| 2005/0085900 | A1 | 4/2005 | Case et al. |
| 2005/0096568 | A1 | 5/2005 | Kato |
| 2005/0096692 | A1 | 5/2005 | Linder et al. |
| 2005/0096724 | A1 | 5/2005 | Stenzel et al. |
| 2005/0096734 | A1 | 5/2005 | Majercak et al. |
| 2005/0096735 | A1 | 5/2005 | Hojeibane et al. |
| 2005/0096736 | A1 | 5/2005 | Osse et al. |
| 2005/0096738 | A1 | 5/2005 | Cali et al. |
| 2005/0107871 | A1 | 5/2005 | Realyvasquez et al. |
| 2005/0113910 | A1 | 5/2005 | Paniagua et al. |
| 2005/0119688 | A1 | 6/2005 | Bergheim |
| 2005/0131438 | A1 | 6/2005 | Cohn |
| 2005/0137686 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Haug et al. |
| 2005/0137695 | A1 | 6/2005 | Salahieh et al. |
| 2005/0137698 | A1 | 6/2005 | Salahieh et al. |
| 2005/0137701 | A1 | 6/2005 | Salahieh et al. |
| 2005/0143807 | A1 | 6/2005 | Pavcnik et al. |
| 2005/0143809 | A1 | 6/2005 | Salahieh et al. |
| 2005/0148997 | A1 | 7/2005 | Valley et al. |
| 2005/0149181 | A1 | 7/2005 | Eberhardt |
| 2005/0165477 | A1 | 7/2005 | Anduiza et al. |
| 2005/0171597 | A1 | 8/2005 | Boatman et al. |
| 2005/0182483 | A1 | 8/2005 | Osborne et al. |
| 2005/0187616 | A1 | 8/2005 | Realyvasquez |
| 2005/0192527 | A1 | 9/2005 | Gharib et al. |
| 2005/0197695 | A1 | 9/2005 | Stacchino et al. |
| 2005/0203549 | A1 | 9/2005 | Realyvasquez |
| 2005/0203605 | A1 | 9/2005 | Dolan |
| 2005/0203618 | A1 | 9/2005 | Sharkawy et al. |
| 2005/0222674 | A1 | 10/2005 | Paine |
| 2005/0228495 | A1 | 10/2005 | Macoviak |
| 2005/0234546 | A1 | 10/2005 | Nugent et al. |
| 2005/0240200 | A1 | 10/2005 | Bergheim |
| 2005/0240263 | A1 | 10/2005 | Fogarty et al. |
| 2005/0261759 | A1 | 11/2005 | Lambrecht et al. |
| 2005/0283962 | A1 | 12/2005 | Boudjemline |
| 2006/0004439 | A1 | 1/2006 | Spenser et al. |
| 2006/0004469 | A1 | 1/2006 | Sokel |
| 2006/0009841 | A1 | 1/2006 | McGuckin, Jr. et al. |
| 2006/0025855 | A1 | 2/2006 | Lashinski et al. |
| 2006/0025857 | A1 | 2/2006 | Bergheim et al. |
| 2006/0047338 | A1 | 3/2006 | Jenson et al. |
| 2006/0052867 | A1 | 3/2006 | Revuelta et al. |
| 2006/0058775 | A1 | 3/2006 | Stevens et al. |
| 2006/0058872 | A1 | 3/2006 | Salahieh et al. |
| 2006/0074484 | A1 | 4/2006 | Huber |
| 2006/0074485 | A1 | 4/2006 | Realyvasquez |
| 2006/0089711 | A1 | 4/2006 | Dolan |
| 2006/0100685 | A1 | 5/2006 | Seguin et al. |
| 2006/0116757 | A1 | 6/2006 | Lashinski et al. |
| 2006/0135964 | A1 | 6/2006 | Vesely |
| 2006/0142848 | A1 | 6/2006 | Gabbay |
| 2006/0149360 | A1 | 7/2006 | Schwammenthal et al. |
| 2006/0167474 | A1 | 7/2006 | Bloom et al. |
| 2006/0178740 | A1 | 8/2006 | Stacchino et al. |
| 2006/0195134 | A1 | 8/2006 | Crittenden |
| 2006/0206192 | A1 | 9/2006 | Tower et al. |
| 2006/0206202 | A1 | 9/2006 | Bonhoeffer et al. |
| 2006/0212111 | A1 | 9/2006 | Case et al. |
| 2006/0247570 | A1 | 11/2006 | Pokorney |
| 2006/0247763 | A1 | 11/2006 | Slater |
| 2006/0253191 | A1 | 11/2006 | Salahieh et al. |
| 2006/0259134 | A1 | 11/2006 | Schwammenthal et al. |
| 2006/0259136 | A1 | 11/2006 | Nguyen et al. |
| 2006/0259137 | A1 | 11/2006 | Artof et al. |
| 2006/0265056 | A1 | 11/2006 | Nguyen et al. |
| 2006/0271166 | A1 | 11/2006 | Thill et al. |
| 2006/0271175 | A1 | 11/2006 | Woolfson et al. |
| 2006/0276874 | A1 | 12/2006 | Wilson et al. |
| 2006/0276882 | A1 | 12/2006 | Case et al. |
| 2006/0282161 | A1 | 12/2006 | Huynh et al. |
| 2007/0005129 | A1 | 1/2007 | Damm et al. |
| 2007/0005131 | A1 | 1/2007 | Taylor |
| 2007/0010876 | A1 | 1/2007 | Salahieh et al. |
| 2007/0010878 | A1 | 1/2007 | Rafiee et al. |
| 2007/0016286 | A1 | 1/2007 | Herrmann et al. |
| 2007/0027518 | A1 | 2/2007 | Case et al. |
| 2007/0027533 | A1 | 2/2007 | Douk |
| 2007/0038295 | A1 | 2/2007 | Case et al. |
| 2007/0043431 | A1 | 2/2007 | Melsheimer |
| 2007/0043435 | A1 | 2/2007 | Seguin et al. |
| 2007/0051377 | A1 | 3/2007 | Douk et al. |
| 2007/0073392 | A1 | 3/2007 | Heyninck-Jantz et al. |
| 2007/0078509 | A1 | 4/2007 | Lotfy |
| 2007/0078510 | A1 | 4/2007 | Ryan |
| 2007/0088431 | A1 | 4/2007 | Bourang et al. |
| 2007/0093869 | A1 | 4/2007 | Bloom et al. |
| 2007/0100439 | A1 | 5/2007 | Cangialosi et al. |

(56) References Cited

U.S. PATENT DOCUMENTS

| | | | |
|---|---|---|---|
| 2007/0100440 | A1 | 5/2007 | Figulla et al. |
| 2007/0100449 | A1 | 5/2007 | O'Neil et al. |
| 2007/0112415 | A1 | 5/2007 | Bartlett |
| 2007/0112422 | A1 | 5/2007 | Dehdashtian |
| 2007/0162102 | A1 | 7/2007 | Ryan et al. |
| 2007/0162113 | A1 | 7/2007 | Sharkawy et al. |
| 2007/0185513 | A1 | 8/2007 | Woolfson et al. |
| 2007/0203391 | A1 | 8/2007 | Bloom et al. |
| 2007/0213813 | A1 | 9/2007 | Von Segesser et al. |
| 2007/0225681 | A1 | 9/2007 | House |
| 2007/0232898 | A1 | 10/2007 | Huynh et al. |
| 2007/0233228 | A1 | 10/2007 | Eberhardt et al. |
| 2007/0233237 | A1 | 10/2007 | Krivoruchko |
| 2007/0233238 | A1 | 10/2007 | Huynh et al. |
| 2007/0238979 | A1 | 10/2007 | Huynh et al. |
| 2007/0239254 | A1 | 10/2007 | Chia et al. |
| 2007/0239265 | A1 | 10/2007 | Birdsall |
| 2007/0239266 | A1 | 10/2007 | Birdsall |
| 2007/0239269 | A1 | 10/2007 | Dolan et al. |
| 2007/0239271 | A1 | 10/2007 | Nguyen |
| 2007/0239273 | A1 | 10/2007 | Allen |
| 2007/0244544 | A1 | 10/2007 | Birdsall et al. |
| 2007/0244545 | A1 | 10/2007 | Birdsall et al. |
| 2007/0244546 | A1 | 10/2007 | Francis |
| 2007/0244553 | A1 | 10/2007 | Rafiee et al. |
| 2007/0244554 | A1 | 10/2007 | Rafiee et al. |
| 2007/0244555 | A1 | 10/2007 | Rafiee et al. |
| 2007/0244556 | A1 | 10/2007 | Rafiee et al. |
| 2007/0244557 | A1 | 10/2007 | Rafiee et al. |
| 2007/0250160 | A1 | 10/2007 | Rafiee |
| 2007/0255394 | A1 | 11/2007 | Ryan |
| 2007/0255396 | A1 | 11/2007 | Donk et al. |
| 2007/0288000 | A1 | 12/2007 | Bonan |
| 2008/0004696 | A1 | 1/2008 | Vesely |
| 2008/0009940 | A1 | 1/2008 | Cribier |
| 2008/0015671 | A1 | 1/2008 | Bonhoeffer |
| 2008/0021552 | A1 | 1/2008 | Gabbay |
| 2008/0048656 | A1 | 2/2008 | Tan et al. |
| 2008/0065011 | A1 | 3/2008 | Marchand et al. |
| 2008/0065206 | A1 | 3/2008 | Liddicoat |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0077234 | A1 | 3/2008 | Styrc |
| 2008/0082165 | A1 | 4/2008 | Wilson et al. |
| 2008/0082166 | A1 | 4/2008 | Styrc et al. |
| 2008/0133003 | A1 | 6/2008 | Seguin et al. |
| 2008/0140189 | A1 | 6/2008 | Nguyen et al. |
| 2008/0147105 | A1 | 6/2008 | Wilson et al. |
| 2008/0147180 | A1 | 6/2008 | Ghione et al. |
| 2008/0147181 | A1 | 6/2008 | Ghione et al. |
| 2008/0147182 | A1 | 6/2008 | Righini et al. |
| 2008/0154355 | A1 | 6/2008 | Benichou et al. |
| 2008/0154356 | A1 | 6/2008 | Obermiller et al. |
| 2008/0161910 | A1 | 7/2008 | Revuelta et al. |
| 2008/0161911 | A1 | 7/2008 | Revuelta et al. |
| 2008/0183273 | A1 | 7/2008 | Mesana et al. |
| 2008/0188928 | A1 | 8/2008 | Salahieh et al. |
| 2008/0021672 | A1 | 9/2008 | Lamphere et al. |
| 2008/0215143 | A1 | 9/2008 | Seguin |
| 2008/0215144 | A1 | 9/2008 | Ryan et al. |
| 2008/0228254 | A1 | 9/2008 | Ryan |
| 2008/0228263 | A1 | 9/2008 | Ryan |
| 2008/0234797 | A1 | 9/2008 | Styrc |
| 2008/0243246 | A1 | 10/2008 | Ryan et al. |
| 2008/0255651 | A1 | 10/2008 | Dwork |
| 2008/0255660 | A1 | 10/2008 | Guyenot et al. |
| 2008/0255661 | A1 | 10/2008 | Straubinger et al. |
| 2008/0262593 | A1 | 10/2008 | Ryan et al. |
| 2008/0269878 | A1 | 10/2008 | Iobbi |
| 2009/0005863 | A1 | 1/2009 | Goetz et al. |
| 2009/0012600 | A1 | 1/2009 | Styrc et al. |
| 2009/0048656 | A1 | 2/2009 | Wen |
| 2009/0054976 | A1 | 2/2009 | Tuval et al. |
| 2009/0069886 | A1 | 3/2009 | Suri et al. |
| 2009/0069887 | A1 | 3/2009 | Righini et al. |
| 2009/0069889 | A1 | 3/2009 | Suri et al. |
| 2009/0082858 | A1 | 3/2009 | Nugent et al. |
| 2009/0085900 | A1 | 4/2009 | Weiner |
| 2009/0099653 | A1 | 4/2009 | Suri et al. |
| 2009/0138079 | A1 | 5/2009 | Tuval et al. |
| 2009/0164004 | A1 | 6/2009 | Cohn |
| 2009/0164006 | A1 | 6/2009 | Seguin et al. |
| 2009/0171447 | A1 | 7/2009 | Von Segesser et al. |
| 2009/0171456 | A1 | 7/2009 | Kveen et al. |
| 2009/0192585 | A1 | 7/2009 | Bloom et al. |
| 2009/0192586 | A1 | 7/2009 | Tabor et al. |
| 2009/0192591 | A1 | 7/2009 | Ryan et al. |
| 2009/0198316 | A1 | 8/2009 | Laske et al. |
| 2009/0216310 | A1 | 8/2009 | Straubinger et al. |
| 2009/0216312 | A1 | 8/2009 | Straubinger et al. |
| 2009/0216313 | A1 | 8/2009 | Straubinger et al. |
| 2009/0222082 | A1 | 9/2009 | Lock et al. |
| 2009/0234443 | A1 | 9/2009 | Ottma et al. |
| 2009/0240264 | A1 | 9/2009 | Tuval et al. |
| 2009/0240320 | A1 | 9/2009 | Tuval et al. |
| 2009/0281619 | A1 | 11/2009 | Le et al. |
| 2009/0287296 | A1 | 11/2009 | Manasse |
| 2010/0004740 | A1 | 1/2010 | Seguin et al. |
| 2010/0030328 | A1 | 2/2010 | Seguin et al. |
| 2010/0036479 | A1 | 2/2010 | Hill et al. |
| 2010/0036485 | A1 | 2/2010 | Seguin |
| 2010/0069852 | A1 | 3/2010 | Kelley |
| 2010/0094411 | A1 | 4/2010 | Tuval et al. |
| 2010/0100167 | A1 | 4/2010 | Bortlein et al. |
| 2010/0131054 | A1 | 5/2010 | Tuval et al. |
| 2010/0137979 | A1 | 6/2010 | Tuval et al. |
| 2010/0145439 | A1 | 6/2010 | Seguin et al. |
| 2010/0152840 | A1 | 6/2010 | Seguin et al. |
| 2010/0161045 | A1 | 6/2010 | Righini |
| 2010/0174362 | A1 | 7/2010 | Straubinger et al. |
| 2010/0198346 | A1 | 8/2010 | Keogh et al. |
| 2010/0234940 | A1 | 9/2010 | Dolan |
| 2010/0256723 | A1 | 10/2010 | Murray |
| 2010/0292785 | A1 | 11/2010 | Sequin et al. |
| 2011/0029066 | A1 | 2/2011 | Gilad et al. |
| 2011/0137397 | A1 | 6/2011 | Chau et al. |

FOREIGN PATENT DOCUMENTS

| | | | |
|---|---|---|---|
| DE | 19532846 | A1 | 3/1997 |
| DE | 19907646 | A1 | 8/2000 |
| DE | 10049813 | C1 | 4/2002 |
| DE | 19546692 | C2 | 11/2002 |
| DE | 10048814 | B4 | 4/2004 |
| DE | 10049812 | B4 | 6/2004 |
| DE | 10010074 | B4 | 4/2005 |
| DE | 19857887 | B4 | 5/2005 |
| DE | 10049815 | B4 | 10/2005 |
| EP | 0103546 | B1 | 5/1988 |
| EP | 144167 | B1 | 11/1989 |
| EP | 0850607 | A1 | 7/1998 |
| EP | 0597967 | B1 | 12/1999 |
| EP | 1057459 | A1 | 12/2000 |
| EP | 1057460 | A1 | 12/2000 |
| EP | 0937439 | B1 | 9/2003 |
| EP | 1340473 | A2 | 9/2003 |
| EP | 1356793 | A2 | 10/2003 |
| EP | 0819013 | B1 | 6/2004 |
| EP | 1229864 | B1 | 4/2005 |
| EP | 1088529 | B1 | 6/2005 |
| EP | 1000590 | B1 | 8/2005 |
| EP | 1469797 | B1 | 11/2005 |
| EP | 1255510 | B1 | 4/2007 |
| EP | 1600121 | B1 | 7/2007 |
| EP | 1472996 | B1 | 9/2009 |
| EP | 2257242 | | 12/2010 |
| FR | 2788217 | A1 | 7/2000 |
| FR | 2815844 | A1 | 5/2002 |
| GB | 2056023 | A | 3/1981 |
| GB | 2398245 | B | 3/2007 |

(56) References Cited

FOREIGN PATENT DOCUMENTS

| | | | |
|---|---|---|---|
| GB | 2433700 | B | 12/2007 |
| SU | 1271508 | A1 | 11/1986 |
| WO | WO 91/17720 | A1 | 11/1991 |
| WO | WO 92/17118 | A1 | 10/1992 |
| WO | WO 93/01768 | A1 | 2/1993 |
| WO | WO 93/15693 | A1 | 8/1993 |
| WO | WO 95/04556 | A2 | 2/1995 |
| WO | WO 95/29640 | A1 | 11/1995 |
| WO | WO 96/14032 | A1 | 5/1996 |
| WO | WO 96/30072 | A1 | 10/1996 |
| WO | WO 98/14137 | A1 | 4/1998 |
| WO | WO 98/29057 | A1 | 7/1998 |
| WO | WO 98/36790 | A1 | 8/1998 |
| WO | WO 99/12483 | A1 | 3/1999 |
| WO | WO 99/33414 | A1 | 7/1999 |
| WO | WO 99/40964 | A1 | 8/1999 |
| WO | WO 99/47075 | A1 | 9/1999 |
| WO | WO 00/09059 | A2 | 2/2000 |
| WO | WO 00/41652 | A1 | 7/2000 |
| WO | WO 00/44308 | A2 | 8/2000 |
| WO | WO 00/44313 | A1 | 8/2000 |
| WO | WO 00/47136 | A1 | 8/2000 |
| WO | WO 00/47139 | A1 | 8/2000 |
| WO | WO 00/67661 | A2 | 11/2000 |
| WO | WO 01/05331 | A1 | 1/2001 |
| WO | WO 01/35870 | A1 | 5/2001 |
| WO | WO 01/49213 | A2 | 7/2001 |
| WO | WO 01/54625 | A1 | 8/2001 |
| WO | WO 01/62189 | A1 | 8/2001 |
| WO | WO 01/64137 | A1 | 9/2001 |
| WO | WO 01/76510 | A2 | 10/2001 |
| WO | WO 01/97715 | A1 | 12/2001 |
| WO | WO 02/22054 | A1 | 3/2002 |
| WO | WO 02/36048 | A1 | 5/2002 |
| WO | WO 02/41789 | A2 | 5/2002 |
| WO | WO 02/43620 | A1 | 6/2002 |
| WO | WO 02/47575 | A2 | 6/2002 |
| WO | WO 02/49540 | A2 | 6/2002 |
| WO | WO 02/060352 | A1 | 8/2002 |
| WO | WO 02/100297 | A2 | 12/2002 |
| WO | WO 03/003943 | A2 | 1/2003 |
| WO | WO 03/003949 | A2 | 1/2003 |
| WO | WO 03/011195 | A2 | 2/2003 |
| WO | WO 03/015851 | A1 | 2/2003 |
| WO | WO 03/028592 | A1 | 4/2003 |
| WO | WO 03/030776 | A2 | 4/2003 |
| WO | WO 03/037227 | A2 | 5/2003 |
| WO | WO 03/094793 | A1 | 11/2003 |
| WO | WO 2004/019811 | A2 | 3/2004 |
| WO | WO 2004/019825 | A1 | 3/2004 |
| WO | WO 2004/023980 | A2 | 3/2004 |
| WO | WO 2004/041126 | A1 | 5/2004 |
| WO | WO 2004/047681 | A1 | 6/2004 |
| WO | WO 2004/058106 | A2 | 7/2004 |
| WO | WO 2004/089250 | A1 | 10/2004 |
| WO | WO 2004/089253 | A1 | 10/2004 |
| WO | WO 2004/093728 | A2 | 11/2004 |
| WO | WO 2004/105651 | A1 | 12/2004 |
| WO | WO 2005/002466 | A2 | 1/2005 |
| WO | WO 2005/004753 | A1 | 1/2005 |
| WO | WO 2005/009285 | A2 | 2/2005 |
| WO | WO 2005/011534 | A1 | 2/2005 |
| WO | WO 2005/011535 | A2 | 2/2005 |
| WO | WO 2005/023155 | A1 | 3/2005 |
| WO | WO 2005/027790 | A1 | 3/2005 |
| WO | WO 2005/046528 | A1 | 5/2005 |
| WO | WO 2006/026371 | A1 | 3/2006 |
| WO | WO 2006/070372 | A2 | 7/2006 |
| WO | WO 2006/076890 | A1 | 7/2006 |
| WO | WO 2007/013999 | A2 | 2/2007 |
| WO | WO 2008/047354 | A2 | 4/2008 |
| WO | WO 2008/100599 | A1 | 8/2008 |
| WO | WO 2008/138584 | A1 | 11/2008 |
| WO | WO 2008/150529 | A1 | 12/2008 |
| WO | WO 2009/002548 | A1 | 12/2008 |
| WO | WO 2009/029199 | A1 | 3/2009 |
| WO | WO 2009/042196 | A2 | 4/2009 |
| WO | WO 2009/045338 | A1 | 4/2009 |
| WO | WO 2009/053497 | A1 | 4/2009 |
| WO | WO 2009/061389 | A2 | 5/2009 |
| WO | WO 2009/091509 | A1 | 7/2009 |
| WO | WO 2009/100198 | A2 | 8/2009 |
| WO | WO 2009/108615 | A1 | 9/2009 |
| WO | WO 2009/111241 | A2 | 9/2009 |
| WO | WO 2010/104638 | A2 | 9/2010 |
| WO | WO 2010/141626 | A2 | 12/2010 |

OTHER PUBLICATIONS

Babaliaros, V. and Block, P., "State of the Art Percutaneous Intervention for the Treatment of Valvular Heart Disease: A Review of the Current Technologies and Ongoing Research in the Field of Percutaneous Heart Valve Replacement and Repair," *Cardiology* 107:87-96 (2007).

Bailey, S., "Percutaneous Expandable Prosthetic Valves," in *Textbook of Interventional Cardiology*, vol. II, Second edition, 1268-1276, E. Topel ed., WB Saunders, Philadelphia, United States (1994).

Block, P., and Bonhoeffer, P., "Percutaneous Approaches to Valvular Heart Disease," *Current Cardiology Reports* 7:108-113 (2005).

Bonhoeffer, P., et al., "Percutaneous Insertion of the Pulmonary Valve," *Journal of the American College of Cardiology* 39(10):1664-1669, United States (May 15, 2002).

Bonhoeffer, P., et al., "Percutaneous Mitral Valve Dilatation with the Multi-Track System," *Catheterization and Cardiovascular Intervention* 48:178-183, United States (Oct. 1999).

Bonhoeffer, P., et al., "Percutaneous Replacement of Pulmonary Valve in a Right-Ventricle to Pulmonary-Artery Prosthetic Conduit with Valve Dysfunction," *The Lancet* 356:1403-1405, England (Oct. 21, 2000).

Bonhoeffer, P., et al., "Technique and Results of Percutaneous Mitral Valvuloplasty With the Multi-Track System," *Journal of Interventional Cardiology* 13(4):263-268, United States (2000).

Bonhoeffer, P., et al., "Transcatheter Implantation of a Bovine Valve in Pulmonary Position: A Lamb Study," *Circulation* 102:813-816, United States (Aug. 15, 2000).

Boudjemline, Y., and Bonhoeffer, P., "Percutaneous Aortic Valve Replacement in Animals," *Circulation* 109:e161, United States, (Mar. 16, 2004).

Boudjemline, Y., and Bonhoeffer, P., "Is Percutaneous Implantation of a Bovine Venous Valve in the Inferior Vena Cava a Reliable Technique to Treat Chronic Venous Insufficiency Syndrome?" *Medical Science Monitor-International Medical Journal of Experimental and Clinical Research* 10(3) :BR61-BR66, Poland, (Mar. 2004).

Boudjemline, Y., et al., "Off-pump Replacement of the Pulmonary Valve in Large Right Ventricular Outflow Tracts: A Hybrid Approach," *The Journal of Thoracic and Cardiovascular Surgery* 129(4):831-837, United States (Apr. 2005).

Boudjemline, Y., et al., "Percutaneous Aortic Valve Replacement: Will We Get There?" *Heart* 86:705-706, British Cardiac Society, England (Dec. 2001).

Boudjemline, Y., et al., "Percutaneous Closure of a Paravalvular Mitral Regurgitation with Amplatzer and Coil Prostheses," *Archives des Maladies du Coeur Et Des Vaisseaux*:483-486, France (May 2002).

Boudjemline, Y., et al., "Percutaneous Implantation of a Biological Valve in Aortic Position: Preliminary Results in a Sheep Study," *European Heart Journal* 22:630 (Sep. 2001).

Boudjemline Y., et al., "Percutaneous Implantation of a Biological Valve in the Aorta to Treat Aortic Valve Insufficiency—A Sheep Study," *Medical Science Monitor-International Medical Journal of Experimental and Clinical Research* 8 (4):BR 113-BR116, Poland (Apr. 2002).

Boudjemline, Y., and Bonhoeffer, P., "Percutaneous Implantation of a Valve in the Descending Aorta in Lambs," *European Heart Journal* 23:1045-1049, England (Jul. 2002).

Boudjemline, Y., et al., "Percutaneous Pulmonary Valve Replacement in a Large Right Ventricular Outflow Tract: An Experimental

(56) References Cited

OTHER PUBLICATIONS

Study," *Journal of the American College of Cardiology* 43(6):1082-1087, United States (Mar. 17, 2004).
Boudjemline, Y., et al., "Percutaneous Valve Insertion: A New Approach?," *The Journal of Thoracic and Cardiovascular Surgery* 125(3):741-742, United States (Mar. 2003).
Boudjemline, Y., et al., "Stent Implantation Combined with a Valve Replacement to Treat Degenerated Right Ventricle to Pulmonary Arter Prosthetic Conduits," *European Heart Journal* 22:355 (Sep. 2001).
Boudjemline, Y., and Bonhoeffer, P., "Steps Toward Percutaneous Aortic Valve Replacement," *Circulation* 105:775-778, United States (Feb. 12, 2002).
Boudjemline, Y., and Bonhoeffer, P., "The Percutaneous Implantable Heart Valve," *Progress in Pediatric Cardiology* 14:89-93, Ireland, (2001).
Boudjemline, Y., et al., "Transcatheter Reconstruction of the Right Heart," *Cardiology in the Young* 13:308-11, England (Jun. 2003).
Coats, L., et al., "The Potential Impact of Percutaneous Pulmonary Valve Stent Implantation on Right Ventricular Outflow Tract Re-Intervention," *European Journal of Cardio-Thoracic Surgery* 27:536-543, England (Apr. 2005).
Commeau, P., et al., "Percutaneous balloon dilatation of calcific aortic valve stenosis: anatomical and haemodynamic evaluation," *British Heart Journal* 59:227-238 (1988).
Cribier, A. et al., "Percutaneous Transcatheter Implantation of an Aortic Valve Prosthesis for Calcific Aortic Stenosis: First Human Case Description," *Circulation* 106:3006-3008 (2002).
Davidson, M., et al., "Percutaneous therapies for valvular heart disease," *Cardiovascular Pathology* 15:123-129 (2006).
Deac, R. et al., "New evolution in mitral physiology and surgery: mitral stentless pericardial valve," *Ann. Thorac. Surg. 60(2 Suppl)*:S433-S438 (Aug. 1995).
Hanzel, G., and O'Neill, W., "Complications of percutaneous aortic valve replacement: experience with the Criber-Edwards™ percutaneous heart valve," *EuroIntervention Supplements I* (*Supplement A*):A3-A8 (2006).
Heinrich, R. et al., "Experimental analysis of fluid mechanical energy losses in aortic valve stenosis: importance of pressure recovery," *Ann. Biomed. Eng.* 24:685-694 (Nov.-Dec. 1996).
Heinrich, R. et al., "Valve orifice area alone is an insufficient index of aortic stenosis severity: effects of the proximal and distal geometry on transaortic energy loss," *J. Heart Valve Dis.* 8(5):509-515, Abstract, (Sep. 1999).
Huber, C., et al., "Do Valved Stents Compromise Coronary Flow?" *Eur. J. Cardiothorac. Surg.* 25:754-759 (2004).
Khambadkone, S., and Bonhoeffer, P., "Percutaneous Implantation of Pulmonary Valves," *Expert Review of Cardiovascular Therapy*:541-548, England (Nov. 2003).
Khambadkone, S., et al., "Percutaneous Pulmonary Valve Implantation: Early and Medium Term Results," *Circulation 108* (*17 Supplement*):IV-375 (Oct. 28, 2003).
Khambadkone, S., et al.,"Percutaneous Pulmonary Valve Implantation: Impact of Morphology on Case Selection," *Circulation 108* (*17 Supplement*):IV-642-643 (Oct. 28, 2003).
Khambadkone, S., and Bonhoeffer, P., "Nonsurgical Pulmonary Valve Replacement: Why, When, and How?" *Catheterization and Cardiovascuiar Interventions* 62:401-408, United States (Jul. 2004).
Lutter, G., et al., "Percutaneous Aortic Valve Replacement: An Experimental Study," *The Journal of Thoracic and Cardiovascular Surgery* 123(9):768-776 (Apr. 2002).
Lutter, G., et al., "Percutaneous Valve Replacement: Current State and Future Prospects," *Annals of Thoracic Surgery* 78:2199-2206, Netherlands (Dec. 2004).
Ma, L. et al., "Double-crowned valved stents for off-pump mitral valve replacement," *European Journal of Cardio-Thoracic Surgery* 28:194-198 (2005).
Marcus, R. et al., "Assessment of small-diameter aortic mechanical prostheses: physiological relevance of the Doppler gradient, utility of flow augmentation, and limitations of orifice area estimation," *Circulation* 98(9):866-872 (Sep. 1, 1998).
"New Frontiers in Heart Valve Disease," *Medtech Insight* 7(8) (Aug. 2005).
Niethspach, F., et al., "Current Balloon-Expandable Transcatheter Heart Valve and Delively Systems," *Catheterization and Cardiovascular Interventions*:1-6 (2009).
Palacios, I., "Percutaneous Valve Replacement and Repair, Fiction or Reality?" *Journal of American College of Cardiology* 44(8):1662-1663 (2004).
Pavcnik, P., et al., "Aortic and venous valve for percutaneous insertion," *Min. Invas. Ther. & Allied Techol.* 9(3/4):287-292 (2000).
Pelton, A.R., et al., "Medical Uses of Nitinol," *Materials Science Forum* 327-328:63-70 (2000).
Ruiz, C.E., "Transcathether Aortic Valve Implantation and Mitral Valve Repair: State of the Art," *Pediatric Cardiology* 26(3):289-294 (2005).
Saliba, Z., et al., "Treatment of Obstructions of Prosthetic Conduits by Percutaneous Implantation of Stents," *Archives des Maldies du Coeur et des Vaisseaux* 92(5):591-596, France (1999).
Stassano, P., et al., "Mid-term results of the valve-on-valve technique for bioprosthetic failure," *Eur. J. Cardiothorac. Surg.* 18:453-457 (2000).
Stein, P., and Sabbah, H.N., "Turbulent blood flow in the ascending aorta of humans with normal and diseased aortic valves," *Circulation Research* 39:58-65, American Heart Association (1976).
Webb, J., et al., "Percutaneous Aortic Valve Implantation Retrograde from the Femoral Artery," *Circulation* 113:842-850 (2006).
Weyman, A., and Scherrer-Crosbie, M., "Aortic Stenosis: Physics and Physiology—What Do the Numbers Really Mean?," *Rev. Cardiovasc. Med.* 6(1):23-32 (2005).
Yonga, G.O., et al., "Effect of Percutaneous Balloon Mitral Valvotomy on Pulmonary Venous Flow in Severe Mitral Stenosis," *East African Medical Journal* 76(1):28-30, Kenya (Jan. 1999).
Yonga, G.O., et al., "Percutaneous Balloon Mitral Valvotomy: Initial Experience in Nairobi Using a New Multi-Track Catheter System," *East African Medical Journal* 76(2):71-74, Kenya (Feb. 1999).
Yonga,G.O., et al., "Percutaneous Transluminal Balloon Valvuloplasty for Pulmonary Valve Stenosis: Report on Six Cases," *East African Medical Journal* 71(4):232-235, Kenya (Apr. 1994).
Yonga, G.O, and Bonhoeffer, P., "Percutaneous Transvenous Mitral Commissurotomy in Juvenile Mitral Stenosis," *East African Medical Journal* 172-174, Kenya, (Apr. 2003).
English Language Abstract of German Patent Publication No. DE 10049812 B4, European Patent Office, espacenet database—Worldwide, (2004) (listed as document FP70 on the accompanying form PTO/SB/08A).
English Language Abstract of German Patent Publication No. DE 10049813 C1, European Patent Office, espacenet database—Worldwide, (2002) (listed as document FP45 on the accompanying form PTO/SB/08A).
English Language Abstract of German Patent Publication No. DE 10049815 B4, European Patent Office, espacenet database—Worldwide, (2005) (listed as document FP91 on the accompanying form PTO/SB/08A).
English Language Abstract of German Patent Publication No. DE 19532846 A1, European Patent Office, espacenet database—Worldwide, (1997) (listed as document FP14 on the accompanying form PTO/SB/08A).
English Language Abstract of German Patent Publication No. DE 19546692 C2, European Patent Office, espacenet database—Worldwide, (2002) (listed as document FP53 on the accompanying form PTO/SB/08A).
English Language Abstract of German Patent Publication No. DE 19857887 B4, European Patent Office, espacenet database—Worldwide, (2005) (listed as document FP87 on the accompanying form PTO/SB/08A).
English Language Abstract of German Patent Publication No. DE 19907646 A1, European Patent Office, espacenet database—Worldwide, (2000) (listed as document FP31 on the accompanying form PTO/SB/08A).

(56) References Cited

OTHER PUBLICATIONS

English Language Abstract of Chinese Patent Publication No. 101011298 A, European Patent Office, espacenet database—Worldwide, (2007) (listed as document FP100 on the accompanying form PTO/SB/08A).
Drawing by Dr. Buller (Edwards Expert) of "higher stent" on the schematic representation of the aortic valve area set out in Figure 2 of Rothman's first expert report, *Corevalve, Inc.* v. *Edwards Lifesciences AG and Edwards Lifesciences PVT, Inc.*, High Court of Justice—Chancery Division Patents Court, United Kingdom, Case No. HC-07-C01243,
Drawing by Dr. Buller (Edwards Expert) of his interpretation of the "higher stent" referred to at col. 8, lines 13-222 of Andersen EP 592410B1, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Expert report of Dr. Nigel Buller, *Edwards Lifesciences AG* v. *Cook Biotech Incorporated*, High Court of Justice—Chancery Division Patents Court, United Kingdom, Case No. HC 08CO0934, dated Jan. 12, 2009.
Expert report of Dr. Nigel Buller, non confidential annex—infringement, *Edwards Lifesciences AG* v. *Cook Biotech Incorporated*, High Court of Justice—Chancery Division Patents Court, United Kingdom, Case No. HC 08CO0934, dated Jan. 12, 2009.
Expert report of Dr. Rodolfo Quijano, *Edwards Lifesciences AG* v. *Cook Biotech Incorporated*, High Court of Justice—Chancery Division Patents Court, United Kingdom, Case No. HC 08CO0934, dated Jan. 9, 2009.
First Expert report of Dr. Anthony C. Lunn, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated Apr. 28, 2008.
First Expert report of Dr. Nigel Person Buller, *Corevalve, Inc.* v. *Edwards Lifesciences AG and Edwards Lifesciences PVT, Inc.*, High Court of Justice—Chancery Division Patents Court, United Kingdom, Case No. HC-07-001243, dated Apr. 28, 2008.
First Expert report of Prof. David Williams, *Edwards Lifesciences AG* v. *Cook Biotech Incorporated*, High Court of Justice—Chancery Division Patents Court, United Kingdom, Case No. HC 08CO0934, dated Jan. 12, 2009.
First Expert report of Prof. Martin Rothman, *Edwards Lifesciences AG* v. *Cook Biotech Court Incorporated*, High Court of Justice—Chancery Division Patents Court, United Kingdom, Case No. HC 08CO0934, dated Jan. 12, 2009.
First Expert report of Professor John R. Pepper, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated Apr. 28, 2008.
First Expert report of Professor Martin Terry Rothman, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated Apr. 28, 2008.
First Expert report of Richard A. Hillstead, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated Apr. 28, 2008.
First Witness statement of Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated May 27, 2008.
Fourth Expert report of Prof. Martin Rothman, *Edwards Lifesciences AG* v. *Cook Biotech Incorporated*, High Court of Justice—Chancery Division Patents Court, United Kingdom, Case No. HC 08CO0934, dated Apr. 22, 2008.
PVT slides naming Alain Cribier, Martin Leon, Stan Rabinovich and Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-C01243.
Reply Expert report of Professor Martin Terry Rothman, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated May 27, 2008.
Reply Expert report of Richard A. Hillstead, *Corevalve, Inc.* v. *Edwards Lifesciences AG and Edwards Lifesciences PVT, Inc.*, High Court of Justice—Chancery Division Patents Court, United Kingdom, Case No. HC-07-001243, dated May 27, 2008.
Second Expert report of Dr. Nigel Buller, *Edwards Lifesciences AG* v. *Cook Biotech Incorporated*, High Court of Justice—Chancery Division Patents Court, United Kingdom, Case No. HC 08CO0934, dated Feb. 25, 2009.
Second Expert report of Dr. Nigel Person Buller, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated May 27, 2008.
Second Expert report of Dr. Rodolfo Quijano, *Edwards Lifesciences AG* v. *Cook Biotech Incorporated*, High Court of Justice—Chancery Division Patents Court, United Kingdom, Case No. HC 08CO0934, dated Feb. 26, 2009.
Second Expert report of Prof. David Williams, *Edwards Lifesciences AG* v. *Cook Biotech Incorporated*, High Court of Justice—Chancery Division Patents Court, United Kingdom, Case No. HC 08CO0934, dated Feb. 5, 2009.
Second Expert report of Prof. Martin Rothman, *Edwards Lifesciences AG* v. *Cook Biotech Incorporated*, High Court of Justice—Chancery Division Patents Court, United Kingdom, Case No. HC 08CO0934, dated Feb. 5, 2009.
Second Expert report of Professor John R. Pepper, *Corevalve, Inc.* v. *Edwards Lifesciences AG and Edwards Lifesciences PVT, Inc.*, High Court of Justice—Chancery Division Patents Court, United Kingdom, Case No. HC-07-C01243, dated Jun. 10, 2008.
Second Witness statement of Stanton Rowe, *Corevalve, Inc.* v. *Edwards Lifesciences AG and Edwards Lifesciences PVT, Inc.*, High Court of Justice—Chancery Division Patents Court, United Kingdom, Case No. HC-07-001243, dated Jun. 20, 2008.
Third Expert report of Dr. Nigel Buller, *Edwards Lifesciences AG* v. *Cook Biotech Incorporated*, High Court of Justice—Chancery Division Patents Court, United Kingdom, Case No. HC 08CO0934, dated Apr. 21, 2009.
Third Expert report of Dr. Rudolfo Quijano, *Edwards Lifesciences AG* v. *Cook Biotech Incorporated*, High Court of Justice—Chancery Division Patents Court, United Kingdom, Case No. HC 08CO0934, dated Apr. 27, 2009.
Third Expert report of Prof. David Williams, *Edwards Lifesciences AG* v. *Cook Biotech Incorporated*, High Court of Justice—Chancery Division Patents Court, United Kingdom, Case No. HC 08CO0934, dated Apr. 22, 2009.
Lutter, et al., "Off-Pump Transapical Mitral Valve Replacement" Eur J Cardiothorac Surg 2009;36: 124-128.

* cited by examiner

TRANSCATHETER VALVE WITH TORSION SPRING FIXATION AND RELATED SYSTEMS AND METHODS

CROSS REFERENCE TO RELATED APPLICATION

This application is a continuation of U.S. patent application Ser. No. 14/156,076, filed Jan. 15, 2014, which is a continuation of U.S. application Ser. No. 12/846,962, filed Jul. 30, 2010, now U.S. Pat. No. 8,652,204, which is incorporated herein by reference in its entirety, and which claims the benefit under 35 U.S.C. § 119(e) of U.S. Provisional Patent Application No. 61/320,111, filed Apr. 1, 2010, which is incorporated herein by reference in its entirety.

FIELD OF THE INVENTION

The invention relates generally to medical devices, systems and methods for use in a body (e.g., in a cardiac system), and more particularly, to devices, systems and methods for minimally invasive native heart valve replacement.

BACKGROUND OF THE INVENTION

Natural heart valves, such as aortic valves, mitral valves, pulmonary valves and tricuspid valves, can become damaged by disease in such a manner that they fail to maintain blood flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure and perfusion of blood through the body. Hence, a heart valve that does not function properly may noticeably impair the function of the heart.

Cardiac valve prostheses are well known in the treatment of heart disease to replace malfunctioning heart valves. Heart valve replacement previously required open-heart surgery with its attendant risk, expense, and extended recovery time. Open-heart surgery also requires cardiopulmonary bypass with risk of thrombosis, stroke and infarction. For some patients, open-heart surgery is not even an option because of a critical condition, advanced age, co-existing infection, or other physical limitations.

Recently, there has been increasing interest in minimally invasive and percutaneous replacement of cardiac valves, typically by way of catheterization. In minimally invasive procedures, a catheter is used to insert a valve in a lumen of a blood vessel via percutaneous entry through a distal blood vessel. Typically, such percutaneous prosthetic valve devices comprise an expandable stent segment, a stent anchoring segment and a flow-regulation segment, such as a biological valve. The expandable stent portion is either self-expandable or expanded using a balloon that is part of a transcatheter delivery system.

A drawback of using a stented valve is that the stent can be difficult to properly position, resulting in a misplaced valve. Additionally, stented valves may also lack sufficient radial strength, which could cause migration after implantation due to forces applied by the blood surrounding the valve in the heart. Therefore, there is a need for improved heart valve prostheses that may be implanted using minimally invasive techniques.

SUMMARY OF THE INVENTION

The invention has advantages over prior devices, systems and methods. The invention mitigates the potential complications of invasive surgery, by applying minimally invasive techniques to replace a damaged or malfunctioning heart valve with a replacement prosthetic heart valve. The invention allows for proper placement of the prosthetic heart valve. The inventive prosthetic heart valve is configured to include an amount of radial force in order to keep the prosthetic heart valve in contact with a body lumen into which the valve is implanted. The inventive prosthetic heart valve also reduces or eliminates sliding or migration of the prosthetic heart valve. One benefit to reducing migration of the prosthetic heart valve is that the device is able to perform its intended function, which allows the heart to function properly. Another benefit of eliminating migration of the prosthetic heart valve is that additional surgeries are not required to repair or replace the valve. One aspect of the invention is a prosthetic valve. The prosthetic valve may comprise: an expandable stent including an inner lumen and having a first and a second end; and a spring attached to the first end of the expandable stent; wherein the expandable stent and the spring can expand radially to a desired diametric configuration in order to anchor the prosthetic valve at an implantation position in a body lumen. The prosthetic valve may further comprise a valvular element disposed in the inner lumen of the expandable stent. The valvular element may comprise at least one leaflet. The prosthetic valve may further comprise a plurality of support arms that are used to attach the spring to the first end of the expandable stent. Each of the plurality of support arms may comprise at least one loop through which the spring extends and is attached to the support arm. The support arms may comprise a material that is more stiff than a material comprising the spring. The support arms may limit the amount of radial expansion of the spring in order to result in a desired diametric configuration of the spring. The spring may comprise a torsion spring. The expandable stent may be sized to fit in a heart valve selected from a group consisting of an aortic valve, a mitral valve, a tricuspid valve, and a pulmonary valve. The spring and the expandable stent may be compressed into a collapsed position for insertion into a sheath for delivery to the implantation position. The prosthetic valve may further comprise a second spring attached to the second end of the expandable stent.

A second aspect of the invention is a prosthetic valve delivery system. The system may comprise: a prosthetic valve, comprising: an expandable stent including an inner lumen and having a first and a second end; a valvular element disposed in the inner lumen of the expandable stent; and a spring attached to the first end of the expandable stent; wherein the expandable stent and the spring can expand radially to a desired diametric configuration once deployed in order to anchor the prosthetic valve at an implantation position in a body lumen; and a sheath comprising a distal end and a lumen in which the prosthetic valve is positioned prior to deployment of the prosthetic valve and out of which the prosthetic valve is deployed at the implantation position. The sheath may be retractable in order to deploy the prosthetic valve.

A third aspect of the invention is a method of implanting a prosthetic valve. The method may comprise the steps of: inserting a system into a body, the system comprising: a prosthetic valve, comprising: an expandable stent including an inner lumen and having a first and a second end; a valvular element disposed in the inner lumen of the expandable stent; and a spring attached to the first end of the expandable stent; wherein the expandable stent and the spring can expand radially to a desired diametric configuration once deployed in order to anchor the prosthetic valve at an implantation position in a body lumen; and a sheath comprising a distal end and a lumen in which the prosthetic valve is positioned prior to deployment of the prosthetic valve and out of which the prosthetic valve is deployed at the implantation position; advancing the system to the implantation position; and deploying the prosthetic valve to the desired diametric configuration to anchor the prosthetic valve at the implantation position. The sheath may be retractable in order to deploy the prosthetic valve. The method may further comprise the step of pulling proximally on the system when the prosthetic valve is partially deployed. The method may further comprise the step of removing the remainder of the system and leaving the prosthetic valve, once deployed, in place.

BRIEF DESCRIPTION OF THE DRAWINGS

The invention will be apparent from the following detailed description of the invention in conjunction with the accompanying drawings, of which.

DETAILED DESCRIPTION OF THE INVENTION

The invention will be described with reference to FIGS. 1-20, wherein like numbers refer to like structures. Those skilled in the art will appreciate that the description herein with respect to the figures is for exemplary purposes only and is not intended in any way to limit the scope of the invention.

Figure 1:
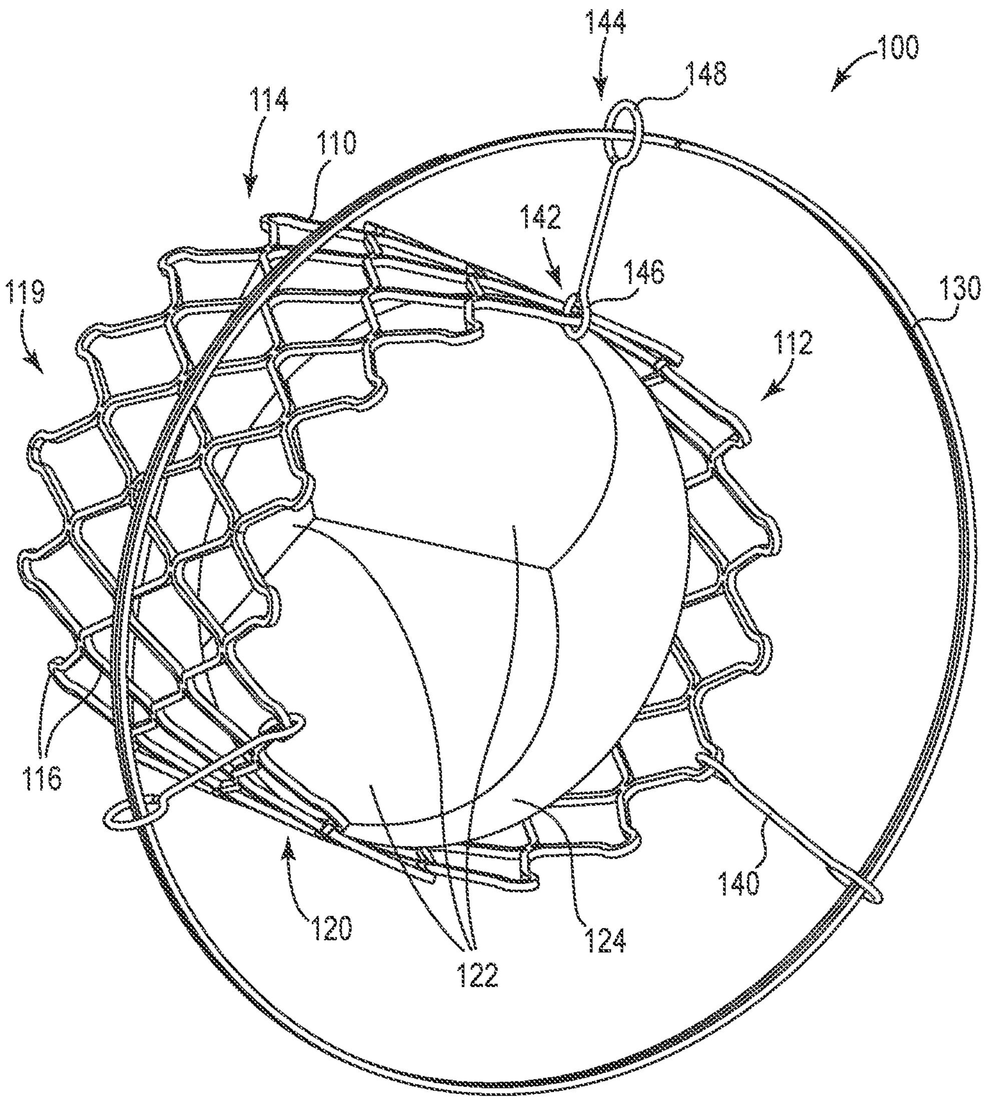
FIG. 1 illustrates a perspective view of an embodiment of a prosthetic heart valve, in accordance with the invention.
Figure 2:
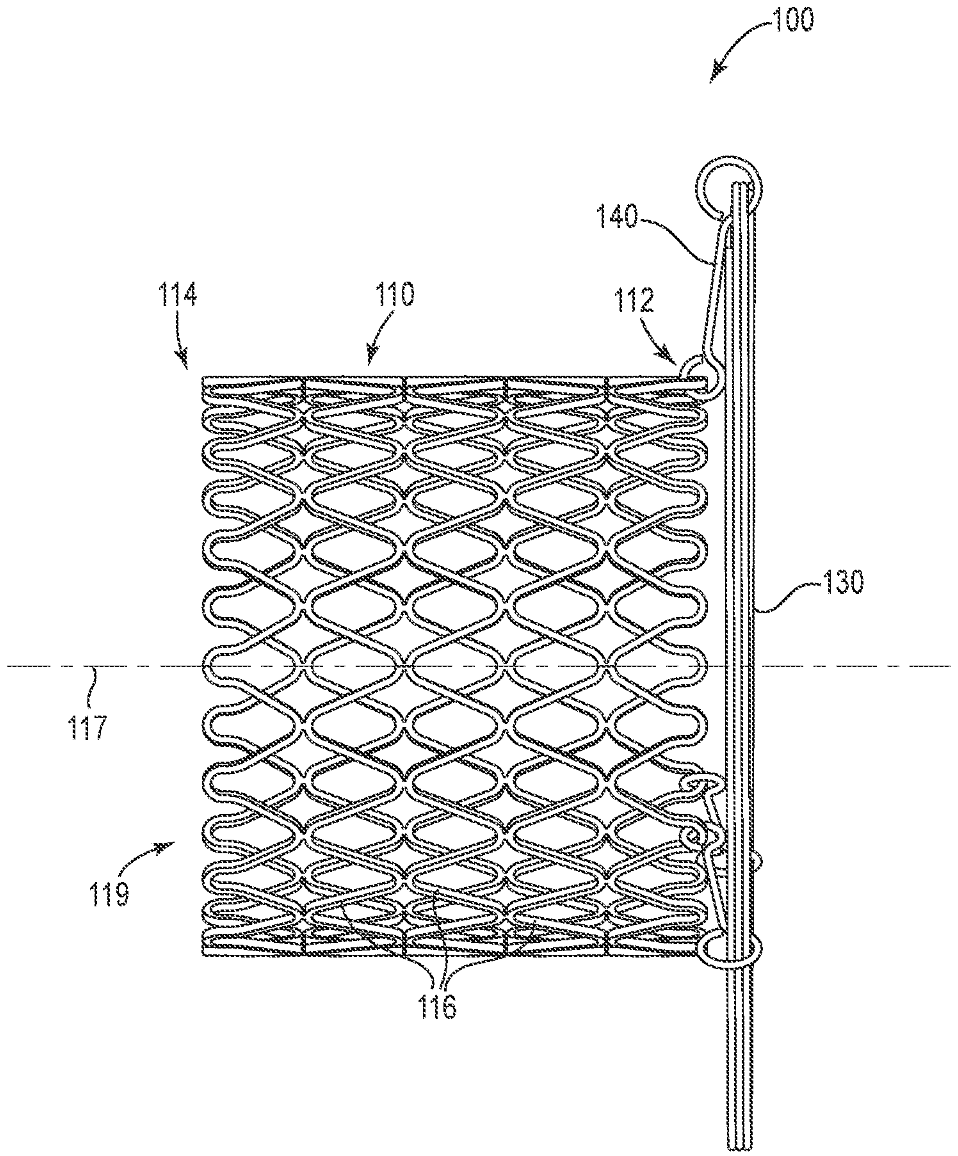
FIG. 2 illustrates a side view of the prosthetic heart valve of FIG. 1.

The invention discloses devices, systems and methods for minimally invasive surgical placement (e.g., via percutaneous catheter placement) of prosthetic heart valves, such as those shown in FIGS. 1 and 2. The invention contemplates that the inventive prosthetic heart valves, systems and methods described herein may be used for replacement of several different heart valves (e.g., mitral valve, tricuspid valve, aortic valve, etc.). More generally, the prosthetic heart valve of the invention may be implanted within a fluid passageway of a body lumen, for example, for replacement or augmentation of a valve structure (e.g., mitral valve), to regulate flow of bodily fluid preferably in a single direction. The invention also contemplates prosthetic valves, in general, that may be used in other suitable locations in the body other than in and near the heart.

One challenge in implanting a prosthetic heart valve within the heart and at a particular annulus is correct placement of the device. Improper placement may cause malfunctioning of the prosthetic heart valve and may require a patient to undergo an additional surgery. The invention addresses this problem by allowing for proper placement of the prosthetic heart valve. In particular, the inclusion of an expandable torsion spring within a prosthetic valve improves the ability to properly place the prosthetic heart valve.

Under certain conditions or due to an improper fit, for example, a prosthetic heart valve may migrate or move after implantation or throughout the life of the prosthetic heart valve due to the forces relating to inflow and backflow of blood flow to and through the prosthetic heart valve. Migration can result in an inadequate seal between the prosthetic heart valve and the wall of the conduit, lumen or vessel, which can further lead to loss of the ability to function effectively. The invention also addresses this problem by inhibiting such migration. Inclusion of an expandable torsion spring within a prosthetic valve for fixation purposes decreases the chances that the prosthetic heart valve will migrate.

Referring to the drawings, FIGS. 1 and 2 show a perspective and a side view, respectively, of an embodiment of a prosthetic heart valve of the invention. Prosthetic heart valve 100, as shown, comprises: an expandable stent 110 including an inner lumen 119 and having a first end 112 and a second end 114; and a spring 130 attached to the first end 112 of the expandable stent 110. The expandable stent 110 and the spring 130 can expand radially to a desired diametric configuration in order to anchor the prosthetic valve 100 at an implantation position in a body lumen. FIG. 1 shows the expanded prosthetic valve 100 including a valvular element 120.

The expandable stent 110 preferably defines a generally cylindrical body having first end 112 and second end 114. However, it is contemplated that the expandable stent 110 can have any geometric shape (e.g., cylindrical, conical, spherical, or barrel-like) that is compatible with the placement of the expandable stent 110 within a body lumen.

The expandable stent 110, once deployed, expands to at least the dimension or diameter of a body lumen into which the expandable stent 110 is implanted. Preferably, the expandable stent, when being used in a mitral valve, can have a diameter or diameters from about five (5) millimeters (mm) to about twenty-five (25) millimeters (mm) based upon typical heart anatomical dimensions. However, other dimensions are also contemplated based upon atypical heart anatomical dimensions as well as based upon different valve annuli (e.g., tricuspid, etc.) into which the prosthetic valve may be implanted.

The expandable stent 110 preferably comprises a mesh. The mesh preferably comprises a plurality of wires 116 or strips that comprise a flexible, biocompatible material. Examples of possible materials for the mesh of the expandable stent 110 include those formed from temperature-sensitive memory alloys, which change shape at a designated temperature or temperature range. Alternatively, the expandable stent 110 can be made from a material having a spring bias. Examples of suitable materials include, but are not limited to, medical grade stainless steel (e.g., 316L), titanium, tantalum, platinum alloys, niobium alloys, cobalt alloys, alginate or combinations thereof. Examples of shape-memory materials include shape memory plastics, polymers, and thermoplastic materials, which are inert in the body. Shape memory alloys having superelastic properties generally made from ratios of nickel and titanium, commonly known as Nitinol™, are preferred materials The preferred material for the plurality of wires 116 will have an adequate amount of stiffness to ensure that the expandable stent 110 maintains a desired shape. The stiffness also needs to be adequate so that the expandable stent 110 maintains a desired shape that ensures that leaflets (as discussed below) in the device 100 close and open properly. Sufficient stiffness also can ensure that there will be no paravalvular leakage; in other words, no leaking between the prosthetic heart valve 100 and the body lumen into which it is implanted. Portions of the expandable stent 110 may be made of different materials and may have different amounts of stiffness.

Various patterns of the plurality of wires 116 in the mesh of the expandable stent 110 are possible. The invention is not limited to the patterns shown herein. The preferred pattern will accommodate the shape of the body lumen or annulus into which the expandable stent 110 will be implanted, as well allow for proper expansion of the expandable stent 110 in the body lumen or annulus.

The plurality of wires 116 of the expandable stent 110 can also have a variety of possible cross-sectional geometries. Examples of cross-sectional geometries include, but are not limited to, rectangular, non-planar configurations, round (e.g., circular, oval and/or elliptical), polygonal, arced and tubular.

The expandable stent 110 of the device 100 is able to be reduced in diameter, mounted in a catheter and advanced through the circulatory system or through other ports or incisions into a patient. The expandable stent 110 is preferably self-expanding. However, it is also possible that the expandable stent 110 may be expanded using a balloon or some other suitable method.

The expandable stent 110 defines a lumen 119 or other housing in which valvular element 120 may be disposed. The valvular element 120 preferably comprises valve leaflets 122 coupled to a valve support 124 that fits in the stent 110, with both components being made of any suitable biocompatible material.

The leaflets 122 and support 124 can be derived from autologous, allogenic, or xenograft material. As will be appreciated, sources for xenograft materials (e.g., cardiac valves) include, but are not limited to, mammalian sources, such as porcine, equine, bovine and sheep. Additional biologic materials from which to form the valve leaflets include, but are not limited to, explanted veins, pericardium, fascia lata, harvested cardiac valves, bladder, vein wall, various collagen types, elastin, intestinal submucosa, and decellularized basement membrane materials, such as small intestine submucosa (SIS), amniotic tissue, or umbilical vein.

Alternatively, the leaflets 122 and support 124 can be formed from a synthetic material. Possible synthetic materials include, but are not limited to, expanded polytetrafluoroethylene (ePTFE), polytetrafluoroethylene (PTFE), polystyrene-poly-isobutylene-polystyrene (SIBS), polyurethane, segmented poly(carbonate-urethane), polyester, polyethylene (PE), polyethylene terephthalate (PET), silk, urethane, rayon, silicone, or the like. In an additional embodiment, the synthetic material can also includes metals, such as stainless steel (e.g., 316L), and Nitinol™. These synthetic materials can be in a woven, a knit, a cast, or other known physical fluid-impermeable or permeable configuration. In addition, plated metals (e.g., gold, platinum, rhodium) can be embedded in the leaflet material (e.g., a sandwich configuration) to allow for visualization of the leaflets 122 post placement.

The leaflets 122 and support 124 can also be formed of any combination of these exemplary materials, or these materials in combination with other materials, as are known in the art. A variety of known treatments and/or coatings can also be included in/on the leaflets 122 and support 124.

The leaflets 122 may comprise a supple and reinforced tissue which is a thickness to be thin enough to occupy the least possible space in the compressed form of the valve, is pliable, and also is strong enough to withstand the unceasing movement under the blood pressure changes during heart beats. The leaflets 122 are capable of moving from a closed position to an open position under the action of the force exerted by the movement of the blood during systole and disastole, without having any significant resistance to blood displacements. The valve leaflets 122 have surfaces defining a reversibly sealable opening for unidirectional flow of a liquid through the prosthetic heart valve 100.

The number of leaflets 122 in the valvular element 120 may be dependent upon the body lumen or annulus into which the prosthetic heart valve 100 is intended to be implanted. For the exemplary embodiment, the valvular element 120 shown in FIG. 1 includes three leaflets 122 for a tri-leaflet configuration. Other configurations including different numbers of leaflets are, however, also contemplated. For example, mono-leaflet, bi-leaflet and/or multi-leaflet configurations are also possible.

The leaflets 122 and the support 124 may be operably attached to the expandable stent 110 by any means known in the art, such that the leaflets 122 can preferably repeatedly move between an open state and a closed state for unidirectional flow of a liquid (e.g., blood) through a lumen of the prosthetic heart valve 100. In one embodiment, the support

124 of the valvular element 120 may be attached to the expandable stent 110 by suturing. Other means for attachment are, however, contemplated by the invention. As one option, the support 124 may be eliminated from the device 100, and the leaflets 122 may be directly attached to the expandable stent 110.

The valvular element 120 may be attached to the expandable stent 120 at any location along its length, as desired for a particular application. In the device shown in FIG. 1, the valvular element 120 is located at or near the middle of the expandable stent 110 (along its length), but other locations are also possible.

As used herein, an undeployed state of the prosthetic heart valve 100 is the state of the prosthetic heart valve 100 at the time the valve is outside the body and as may be provided on a delivery device (e.g., on a catheter or a sheath), and a deployed state is the state of the prosthetic heart valve 100 at the time the prosthetic heart valve 100 is to be left in the body.

As discussed herein, a prosthetic heart valve implanted to replace, for example, a mitral valve, can be difficult to place properly in a mitral valve annulus. In addition, if improperly positioned or sized, a prosthetic heart valve can move or migrate due to the forces acted upon the valve by surrounding blood. Spring 130 is attached to the first end 112 of the expandable stent 110 thereby to assist in proper placement and to reduce the likelihood that the prosthetic heart valve 100 will migrate after the prosthetic heart valve 100 is delivered and implanted at a delivery site, as well as throughout the life of the prosthetic heart valve 100.

The spring 130, shown in FIGS. 1 and 2, comprises a wire that is wound or coiled such that the spring 130, when expanded, has a generally circular shape. Other numbers of wires and other configurations of the spring 130 are, however, also contemplated by the invention. For example, there may be a different number of times that the spring 130 coils or is wound around a central axis 117. In addition, the distance between individual coils (or times the wire is wound around the central axis) of the spring 130 may be varied. The individual coils or times the spring 130 is wound are shown in FIG. 1 as being in direct or close contact to each other. However, alternative configurations are also contemplated in which more space between the individual coils is found in an expanded configuration of the spring 130 (not shown).

The preferred spring 130 is a torsion spring. While not wishing to be bound by theory, a torsion spring is a spring that works by torsion or twisting; that is, a flexible, elastic object that stores mechanical energy when it is twisted. The amount of force (torque) it exerts is proportional to the amount it is twisted. The spring 130 is able to exert force radially against a body lumen into which it is implanted, in order to hold the prosthetic heart valve 100 in place inside the body lumen.

The spring 130 preferably comprises a shape memory material, as those described above with regard to the expandable stent 110. However, other materials are also contemplated by the invention.

The spring 130 is preferably provided as a coil and is wound and radially compressed when the prosthetic heart valve 100 is undeployed and located within a delivery device (e.g., a sheath or catheter). Winding the spring 130 up allows the diameter of the spring 130 to be reduced in order to fit in a delivery device. When the prosthetic heart valve 100 is deployed, the spring 130 will expand to a predetermined diameter in order to contact tissue, or an inner surface of a body lumen, and hold the device 100 in place. While not wishing to be bound by theory, compressed torsional energy in the undeployed device is used to change the diameter of the spring 130 from a small diameter state (during delivery) to a large delivery state (following delivery). The preferred diameter of the small diameter state is less than about 9.3 mm (28 French) and the preferred diameter of the large delivery state of the spring 130 is about 2 cm to about 5 cm, depending upon the expansion of the expandable stent portion 120 or the valve support 124 or frame. Alternatively, the diameter of the larger delivery state can be determined based upon the diameter of the expandable stent portion in its expanded configuration. Preferably, the larger delivery state of the spring 130 could then have a diameter that is between about 0 cm to about 1 cm larger than the larger delivery state diameter of the expandable stent portion.

The material comprising the spring 130 and the configuration of the spring 130 preferably ensures adequate radial stiffness of the spring 130 for a given application. In the embodiment shown, the spring 130 is configured to ensure that there will be sufficient contact between the prosthetic heart valve 100 and the body lumen (i.e., a sufficient fit) into which the prosthetic heart valve 100 fits (e.g., a mitral valve annulus). The fit minimizes the chance of migration of the prosthetic heart valve 100 as forces are applied to the prosthetic heart valve 100 by surrounding blood. The presence of the spring 130 also may eliminate the need to anchor the device 100 into tissue by using, for example, barbs or hooks. Beneficially, the prosthetic heart valve 100 may be used without penetrating tissue of the heart in order to hold the valve 100 in place.

Figure 21:
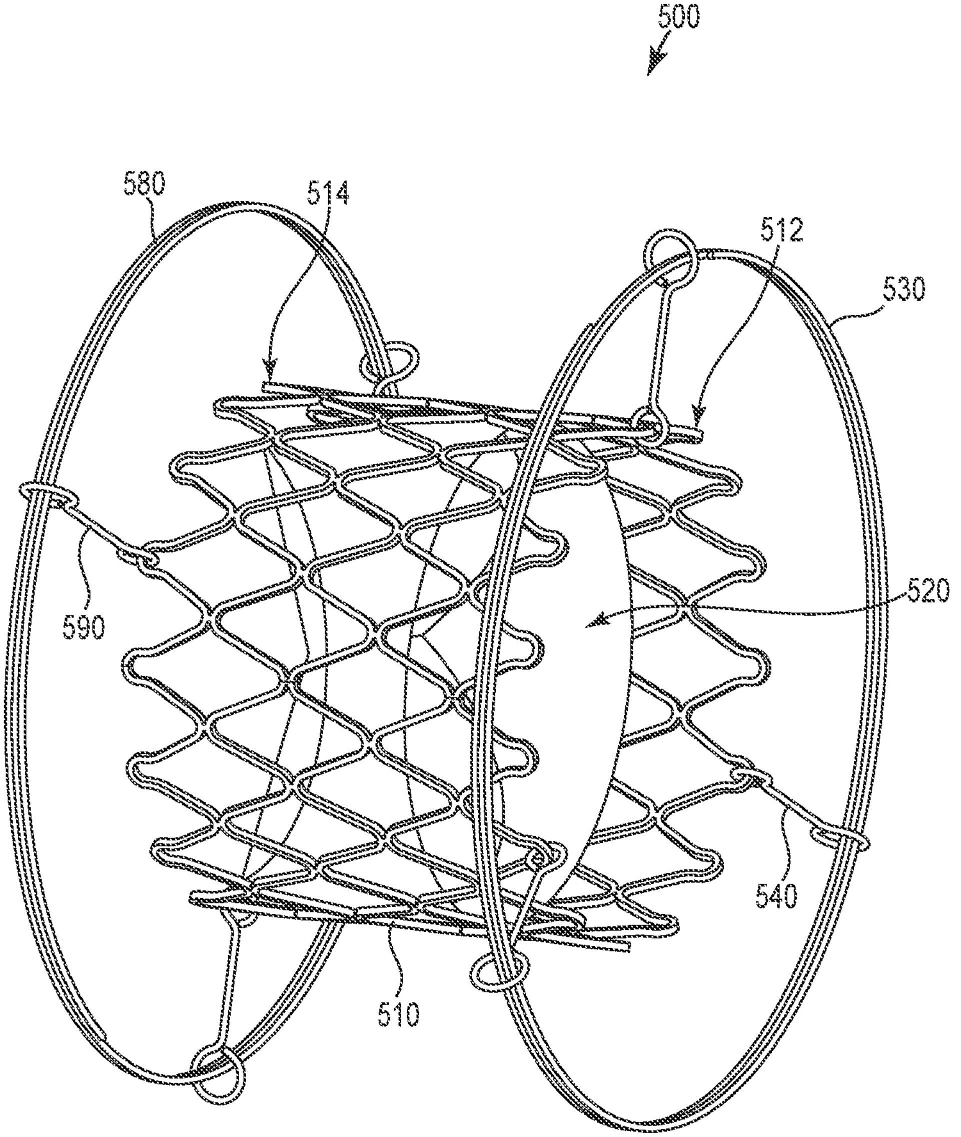
FIG. 21 illustrates a perspective view of an embodiment of a prosthetic valve, of the invention, including two springs.

As an alternative, in another embodiment, there may be springs located on both the first and the second end of the expandable stent. FIG. 21 illustrates this alternative prosthetic heart valve 500. The device 500 preferably includes corresponding features, e.g., expandable stent portion 510 with first end 512 and second end 514, valvular element 520 and first spring 530 with support arms 540. However, a second spring 580 is attached to the second end 514 of the expandable stent portion 510 using support arms 590. The addition of the second spring 580 may provide additional resistance against migration of the prosthetic heart valve 500, or resistance against migration in a different direction from that provided by the first spring 530. Therefore, it is contemplated that the prosthetic heart valve of the invention may include more than one spring.

Depending upon the location of the spring or springs in the prosthetic heart valve of the invention, migration in one or more directions may be prevented. For example, in the embodiment shown in FIGS. 1 and 2, the spring 130 is preferably implanted on the atrial side of the mitral valve annulus, and the remainder of the expandable stent 110 extends through the annulus and into the left ventricle. As a result, the prosthetic heart valve 100, upon implantation, prevents migration of the prosthetic heart valve 100 from the left atrium and into the left ventricle. However, if a second spring would be included and implanted on the ventricular side of the mitral valve annulus, then migration of the prosthetic heart valve from the left ventricle and into the left atrium would also be prevented.

If one spring 130 is used on the prosthetic heart valve 100, as in FIGS. 1 and 2, a flare or anchor (not shown) may be optionally included on the opposite end of the expandable stent portion 110 from the spring 130. The purpose of such flares or such anchors would be to preferably anchor the second end 114 of the expandable stent portion 110 (but also could anchor the first end 112) into tissue opposite (or adjacent) the spring 130. Instead of anchoring into tissue (e.g., by using barbs), it may be possible that the location and design of the anchors would contact the side of the valve annulus opposite the side including the spring 130 without penetrating tissue.

Figure 22:
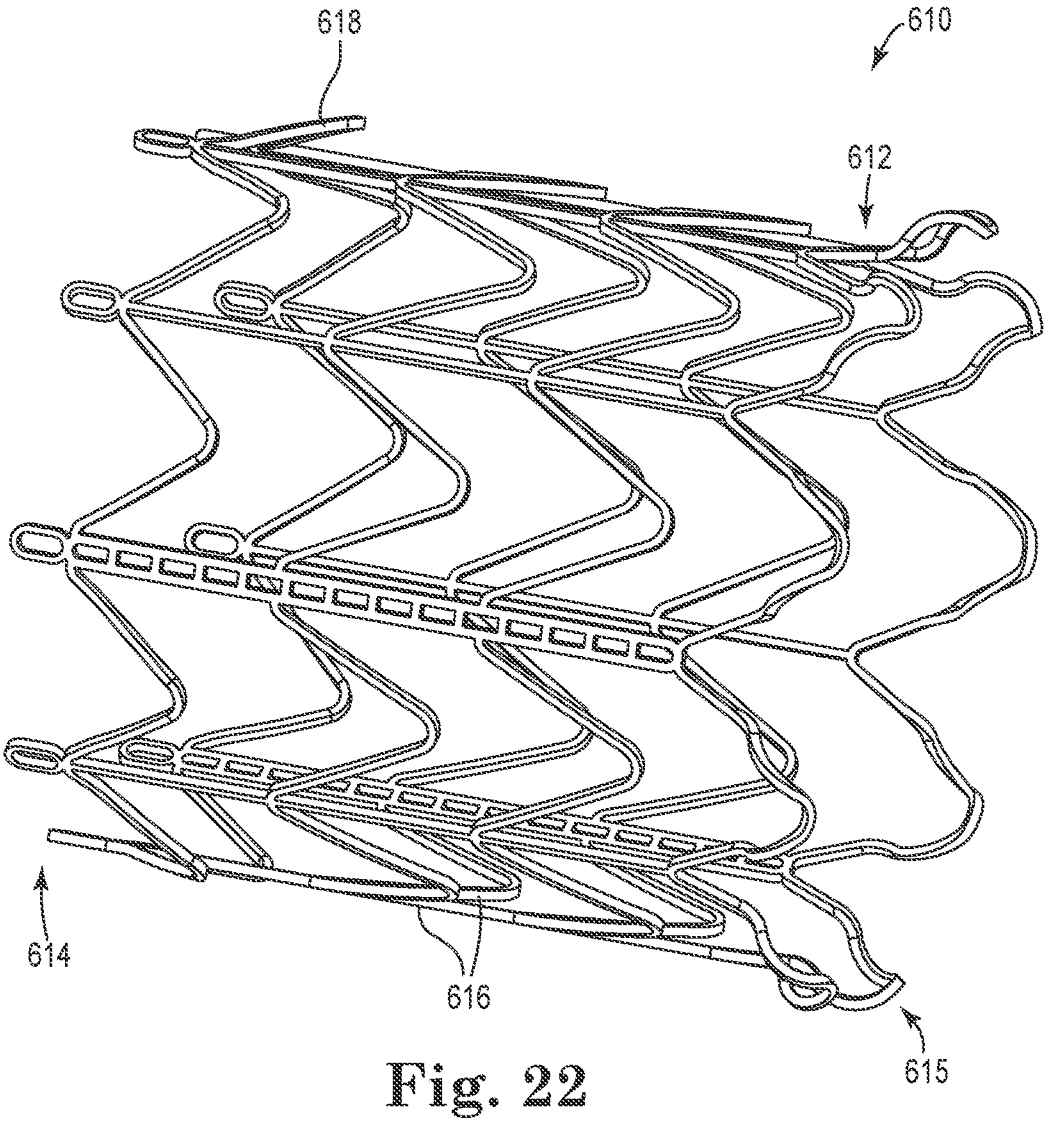
FIG. 22 illustrates a perspective view of an expandable stent portion of an embodiment of a prosthetic valve, in accordance with the invention, including an anchor.

In one example of anchoring the stent, the entire end of the stent could be flared, as shown by 615 in FIG. 22, to a larger diameter. The flare 615 could, however, be on the second end 614 of the stent portion 610 alternatively. Any suitable type of flare, in addition to the flare 620 shown in FIG. 22, is contemplated for use with prosthetic heart valve 100.

One example of a type of anchor that may be used is also illustrated in FIG. 22. FIG. 22 shows an alternative expandable stent portion 610. At or near the second end 614 of the stent portion 610, which will be opposite the first end 612 that is intended to be attached to a spring, one or more anchors 618 will be present. In the embodiment shown, the anchor 618 is actually a flared portion of one of the plurality of wires 616 or members that make up for the expandable stent portion 610. Preferably, there are at least three of these anchors 618 per expandable stent portion 610, but any suitable number is contemplated. The anchor 618 shown in FIG. 22 is, however, only one exemplary anchor. Other anchors are contemplated, which may, for example, include a separate anchoring system that is not part of the stent portion. If the anchoring system is separate, the system may be employed during deployment of the prosthetic heart valve of the invention or may be included post-implant. Some additional examples of such anchors include, but are not limited to, U-clips and sutures.

In the preferred embodiment, shown in FIG. 1, in order to connect the spring 130 to the expandable stent 110, a plurality of support arms 140 are preferably used, although other suitable means for attachment are also contemplated. The support arms 140 are preferably pivotable, rotatable, or otherwise moveable or maneuverable in order to allow the spring 130 and expandable stent 110 to expand to its desired diametric configuration without restriction. The length of the support arms 140 can control the amount of diametric or radial expansion of the spring 130 due to their length. Thus, the length of the support arms 140 will be dependent upon the use of the prosthetic heart valve and desired deployed diameter of the spring 130. Shorter support arms 140 will limit the amount of unwinding of the spring 130 and longer support arms 140 will allow for more expansion of the spring 130. The amount of expansion of the spring 130, therefore, can relate to the length of the supports arms 130 as well as other factors.

As shown in FIG. 1, the support arms 140 are connected at a first end 142 of the support arms 140 to the expandable stent 110 by a loop or eyelet 146 formed by the wire comprising the support arm 140 itself. However, other means for attaching the support arms 140 to the expandable stent 110 are also contemplated. For example, a means for attaching the support arms 140 to the expandable stent 110 that allows the support arms 140 to pivot with respect to the expandable stent 100 is a possible embodiment. Preferably, the support arms 140 are attached to the expandable stent 110 around the circumference of the first end 112 of the expandable stent 110. Preferably, the support arms 140 are generally evenly spaced around the circumference of the first end 112 of the expandable stent 110, however other spacings are also contemplated.

The support arms 140 are attached to the spring 130 at a second end 144 of each support arm. Preferably, and as shown, loops or eyelets 148 are located on the second ends 144 of the support arms 140 through which the spring 130 extends. The spring 130 is preferably able to slide through the loops or eyelets 148 on the support arms 140 in order for the spring 130 to be deployed or expanded. However, other suitable means for attachment to the spring 130 are also contemplated by the invention such that the spring 130 is able to unwind as needed.

The support arms 140 preferably comprise a shape memory material, such as those provided above with regard to the expandable stent 110. A preferred material is Nitinol™. However, other materials are also contemplated by the invention.

Preferably, the stiffness or rigidity of the material used to form the support arms 140 is generally greater than the stiffness or rigidity of the material used to form the spring 130. The relative stiffnesses allows the support arms 140 to maintain a desired expanded diametric configuration of the spring 130 after the device 100 is deployed and undergoes forces within a beating heart, for example. Other relative stiffnesses of the support arms 140 and spring 130, however, are also contemplated by the invention.

The number of support arms 140 may vary, according to the invention. Three support arms 140 are shown in the figures. However, it is contemplated that other numbers of support arms 140 are possible, such that the support arms 140 are able to sufficiently hold the spring 130 in its desired expanded diametric configuration.

The support arms 140 shown are generally linear in shape. However, other shapes are also contemplated that may control deployment of the spring 130. For example, another possible embodiment of the prosthetic heart valve may include a plurality of support arms that when deployed are curved. For example, a deployed prosthetic heart valve may include a plurality of support arms that are all similarly curved. A potential benefit of using curved support arms is that if they collapse, the arms will collapse radially rather than axially. Other shapes and configurations of the support arms are also contemplated.

The number of loops 148 and location of the loops 148 on the support arms 140 may be varied. For example, additional loops may be found along the length of the support arms 140 (not shown). The spring 130 may also be extended through the additional loops. The addition of more loops may be for the purpose of preventing kinking, tangling or twisting of the spring or to better control expansion of the spring to its desired diametric configuration, for example.

Preferably, when the support arms 140 are fully extended and the spring 130 is released to its desired expanded diameter, the support arms 130 will extend generally or nearly perpendicular to a central, longitudinal axis 117 of the expandable stent 110. In FIGS. 1 and 2, the support arms 140 do not extend exactly perpendicular to central axis 117. It is contemplated that the support arms 140 may extend at various angles with respect to the central, longitudinal axis 117 of the expandable stent 110, as desired for a particular application.

As will be appreciated, the prosthetic heart valve 100 can be treated and/or coated with any number of surface or material treatments. Examples of such treatments include, but are not limited to, bioactive agents, including those that modulate thrombosis, those that encourage cellular in-growth, through-growth, and endothelization, those that resist infection, and those that reduce calcification.

Figure 3:
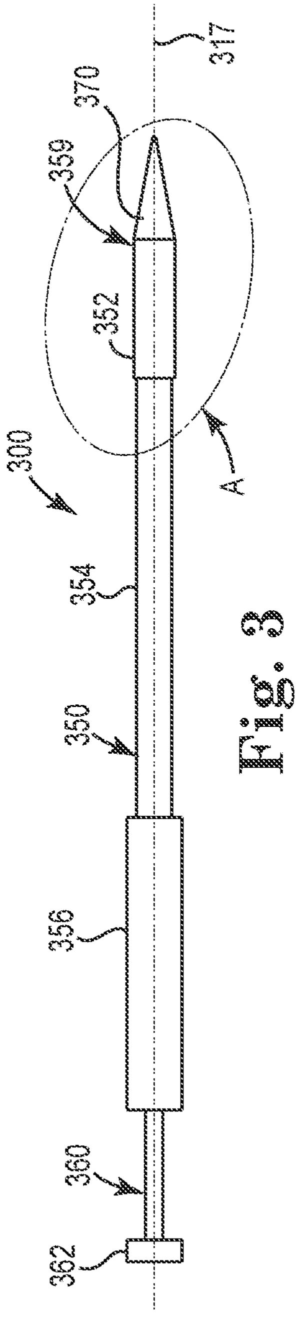
FIG. 3 illustrates a side view of a system, in accordance with the invention.
Figure 4:
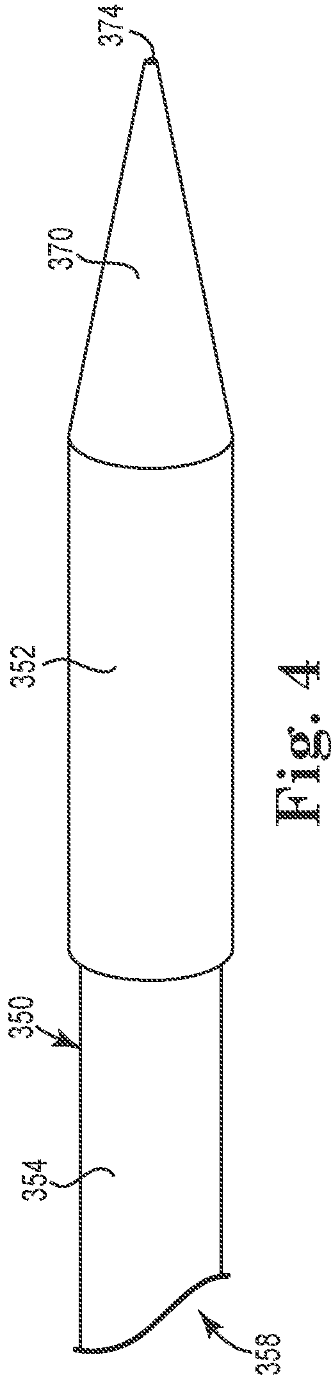
FIG. 4 illustrates a perspective view of distal end portion A of the system shown in FIG. 3.
Figure 5:
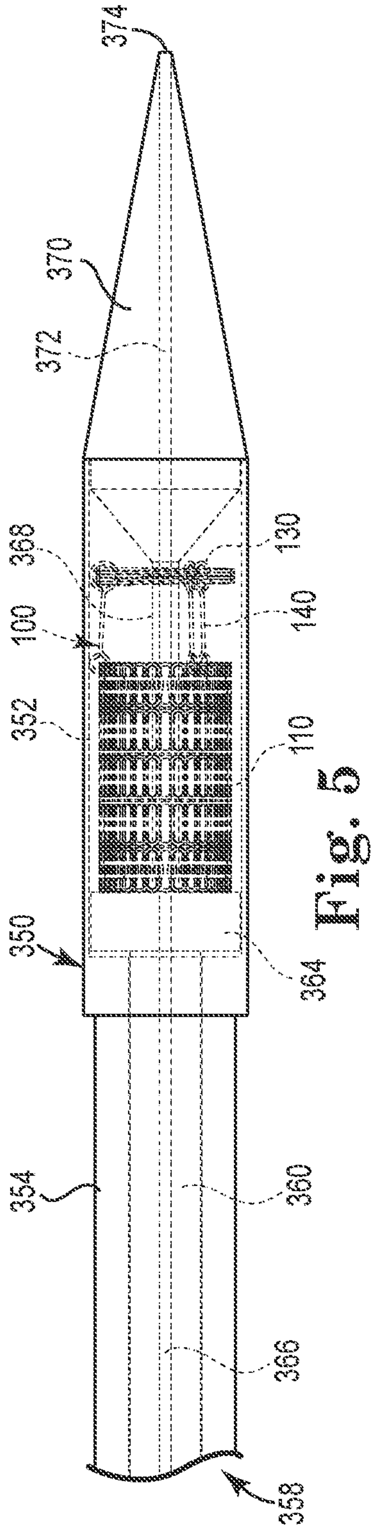
FIG. 5 illustrates a side view of distal end portion A of the system shown in FIG. 3, with interior shown in shadow.

The prosthetic heart valve 100 described above, or other embodiments of the invention, may be a part of a system for replacement of a native valve with a prosthetic heart valve. FIG. 3 illustrates an embodiment of such a system 300 of the invention. The system 300 shown encloses the prosthetic heart valve 100, as described above, or other such prosthetic heart valve in accordance with the invention, in order to deliver the valve to its desired location in a body lumen. The system 300 shown is one embodiment, and other suitable systems are also contemplated. FIGS. 4 and 5 illustrate a distal end portion of system 300, with the distal end indicated in FIG. 3 by the circled portion that is labeled as A. FIG. 4 illustrates a perspective view of distal end A and FIG. 5 illustrates a side view of distal end A, with a collapsed, or non-deployed prosthetic heart valve 100 shown in shadow in the interior of an elongate sheath 350.

System 300 is exemplary, but includes elongate sheath 350 having an inner lumen 358 running along the length of the sheath 350. The sheath 350 is shown as having multiple portions 352, 354, 356 with different diameters. However, it is contemplated that the sheath 350 may have only one diameter, or other numbers of diameters along its length. Preferably, the sheath 350 or portions of the sheath will have a diameter of about five (5) millimeters (mm). Most preferably, the diameter of the sheath 350 is less than about 10 mm (30 French).

In order to deploy the device, preferably the sheath 350 is withdrawn or retracted, which allows the device 100 to expand. As described above, the sheath 350 may have multiple portions, e.g., 352, 354, 356. One alternative embodiment provides for only sheath portion 352 to be withdrawn in order for the device 100 to be deployed. Sheath portion 354 would remain stationary in that embodiment. For example, sheath portion 352 may be withdrawn using actuators that are linear or coaxial on the pushing rod or handle of the system 100.

System 300 also includes a pushing rod 360 that extends into the inner lumen 358 of the sheath 350. The pushing rod 360 has a proximal end 362 that prevents the rod from completely extending into the inner lumen 358. The proximal end also is preferably able to be held by an operator of the system 300. At the opposite end of the pushing rod 360, is a distal end 364. The distal end 364 of the pushing rod 362 is preferably placed against the second end 114 of prosthetic heart valve 100, for example. In order for the prosthetic heart valve 100 to be deployed from sheath 350, the distal end 364 of the pushing rod 360 is held against the device 100, and the sheath 350 is withdrawn or retracted, which results in the device 100 exiting the distal end 359 of sheath 350, and, ultimately, being deployed from the system 300 (as shown in later figures).

The pushing rod 360 also preferably includes an inner lumen 366 (FIG. 5) through which a guide wire or other guiding mechanism for the system 300 may extend. The use of a guide wire (not shown) with the system 300 is preferred, but is not required. The guide wire may also be considered an elongate delivery catheter.

The system 300 also preferably includes a dilator 370 on or near the distal end 359 of sheath 350. The dilator 370 is used to dilate a body lumen or tissue through which the system 300 is desired to extend or penetrate. The dilator 370 is not required, however, and the system 300 may not include one. The preferred dilator 370, however, includes an inner lumen 372 such that the optional guide wire discussed above may also extend through dilator 370 and out an end opening 374 of the dilator 370. If the dilator 370 is included, the pushing rod 360 preferably will include an extension 368 having a preferably narrower diameter that connects the pushing rod 360 to the dilator 370, or the dilator may be otherwise attached to the pushing rod 360. Preferably, the dilator 370 remains stationary with the pushing rod 360 while the sheath 350 is withdrawn or retracted, allowing the device 100 to exit the sheath 350. In another alternative embodiment, a dilator could actuate independent from the remainder of the delivery system.

FIG. 5 shows, in shadow, how the prosthetic heart valve 100 preferably looks prior to deployment. The prosthetic heart valve 100 is shown in a folded, collapsed or undeployed position and inserted into sheath 350 for delivery to an implantation position in a body lumen or annulus. The sheath 350 is positioned to releasably hold the prosthetic heart valve 100 in a delivery, or undeployed, state. The spring 130 is shown more tightly coiled than when deployed. The support arms 140 are extending generally parallel to a central axis 317 of the system 300. The prosthetic heart valve 100 is preferably loaded in the system 300 such that the extension 368 of the pushing rod 360 extends through the inner lumen 119 of the prosthetic heart valve 100, as shown.

The length of pushing rod 360 is shown for purposes of illustration only. Depending upon the application of the system 300, the length of the pushing rod 360 and sheath 350 may be varied. The invention contemplates other lengths.

The system 300 shown in FIG. 3 is one embodiment of the inventive system. Rather than a pushing rod and sheath configuration, it is contemplated that other means for deploying a prosthetic heart valve of the invention are possible. For example, a retractable sheath surrounding the prosthetic heart valve 100 may be used instead. Any suitable means for delivery of the prosthetic heart valve 100 is contemplated.

The sheath 350 can include an inner lining (not shown) on an inner surface of the sheath 350. An inner lining can decrease friction between the prosthetic heart valve device 100 and the sheath 350 while also sealing the sheath 350. The inner lining can be formed of, for example, nylon, Dacron™, expanded polytetrafluoroethylene (ePTFE), and/or other materials.

The sheath 350 can have many possible configurations. For example, in some embodiments, the sheath 350 can be a flexible tube formed of a metal, metal-alloy, and/or polymers, such as polyvinyl chloride, polyethylene, polyethylene terephalate, polyamide, mixtures, and block-copolymers thereof.

The pushing rod 360 and dilator 370 may be formed, for example, by similar materials to those used for the sheath 350. The guide wire may be made of conventional materials. The invention does, however, contemplate that any suitable materials may be used for the components of the system 300.

The valve replacement system 300 will be used in a description below of an inventive method for replacement of a heart valve. Specifically, the method described may be used to deliver prosthetic heart valve 100 to a mitral valve, for example. However, it will be understood from the following description that the invention could be used instead to replace any heart valve or other suitable valve in a body lumen or valve annulus.

To implant the prosthetic heart valve 100, for example, the prosthetic heart valve 100, as described above, is compressed into its collapsed position and inserted into the sheath 350 that has a suitably sized lumen for accepting the compressed prosthetic heart valve 100 (as shown in FIG. 5). The system 300 may be supplied with the prosthetic heart valve 100, for example, already loaded, or instead may require that an operator load the device.

The sheath 350, including the prosthetic heart valve 100, is then guided in the conventional fashion (with or without the use of a guide wire) or advanced to a position adjacent an implantation position in a patient's heart (for example, adjacent the mitral valve annulus). The sheath 350 is preferably delivered to or deployed at a pre-selected position in an anatomical lumen of the heart. The pre-selected position may be, for instance, in proximity to the original location of a natural heart valve.

One preferred method of delivering a prosthetic heart valve to a body lumen includes introducing a mitral valve prosthetic heart valve device, such as prosthetic heart valve 100, to the mitral valve annulus using minimally invasive techniques. Preferably, the heart is off-pump. Preferably, a lower mini-sternotomy or thoracotomy is performed and a standard transapical approach is used for placement of a mitral valve prosthetic heart valve device. However, other anatomical approaches and surgical methods are contemplated for the inventive system 300.

Figure 18:
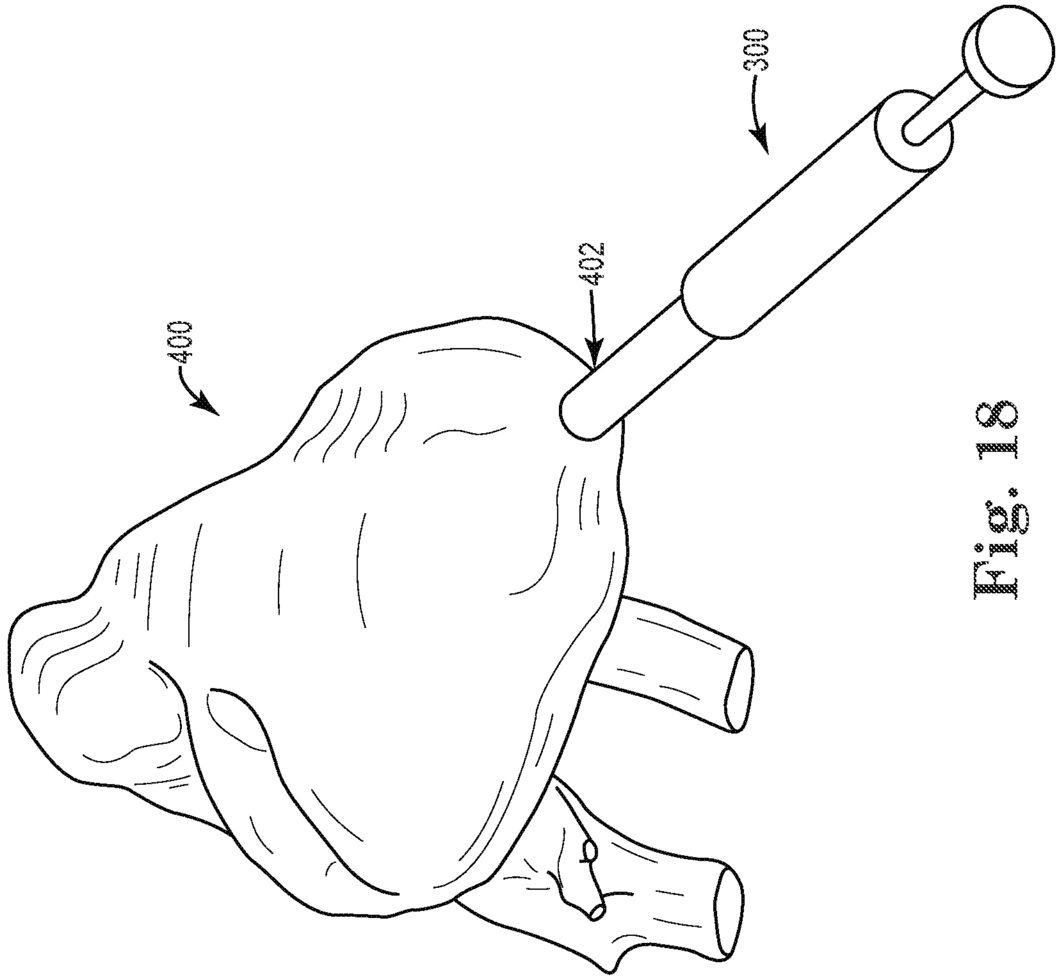
FIG. 18 illustrates a heart with the inventive system being inserted into the apex of the heart.

FIG. 18 shows the system 300 inserted into a heart 400 via a transapical approach. In the figure, the system 300 is partially inserted into an opening 402 made in the apex of the heart 400. The opening 402 is made by puncturing the apex of the heart with the distal end of system 300 or using another instrument prior to introduction of the system 300.

The initial step of inserting or introducing and advancing the system 300 to a desired location, such as into the apex of the heart, as described above, may preferably be done using the aid of a fluoroscope or some other image guidance, in order to view the placement within the body. Imaging devices (not shown) may be used to permit the surgeon (operator) to watch and guide the movement of the prosthetic heart valve device to the implantation position. Some possible image guidance include, but are not limited to, fluoroscopy, ultrasonic means, magnetic resonance, X-ray, computer tomography, and combinations thereof.

Preferably, the prosthetic heart valve 100 includes materials that are radiopaque so that the device can be viewed using imaging devices. For example, a plurality of radiopaque markers may be disposed on the stent and/or coil portions of the device. Radiopaque markers may include radiopaque metals such as, for example, gold and platinum. Examples of suitable radiopaque that may be added to polymeric materials in the device include, but are not limited to, barium sulfate and bismuth sub-carbonate.

Figure 6:
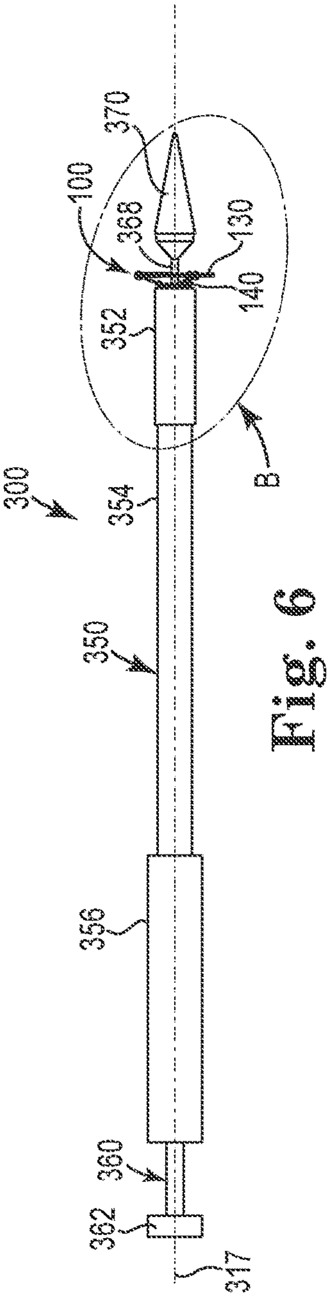
FIG. 6 illustrates a side view of the system of FIG. 3 at a later stage in delivery of a prosthetic heart valve of the system.

Next, once the system 300 is in its desired location in the body, the pushing rod 360 is pushed in a distal direction. FIG. 6 shows the system 300 as the prosthetic heart valve 100 is just beginning to be deployed from the distal end 359 of sheath 350. As illustrated, the spring 130 and support arms 140 have exited the sheath 350 and the spring 130 appears in its desired partially expanded configuration. The support arms 140 are generally perpendicular to a central, longitudinal axis 317 extending though the system 300. The expandable stent 110 of the prosthetic heart valve 100 has not yet completely exited the sheath 450.

Figure 7:
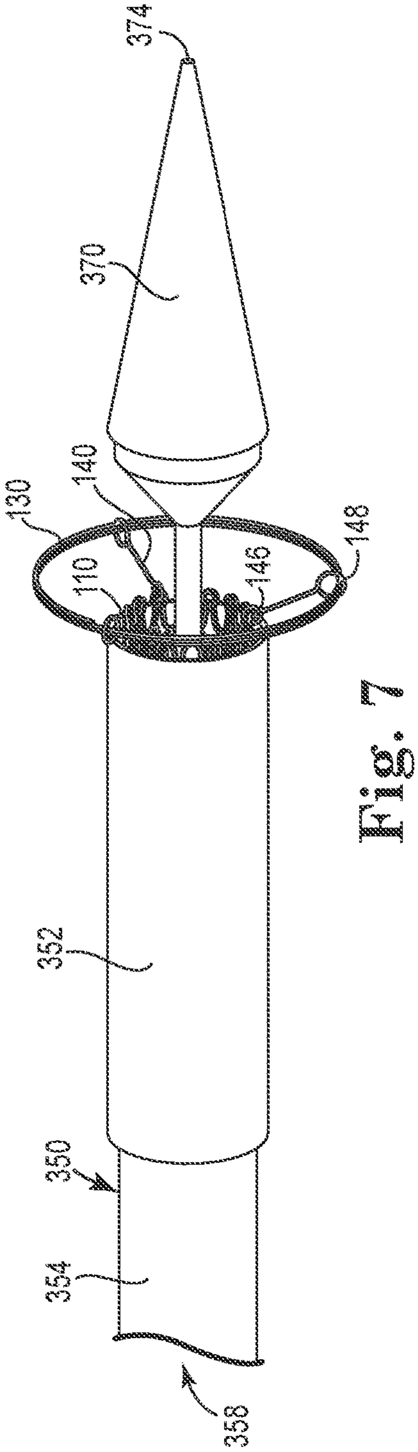
FIG. 7 illustrates a perspective view of distal end portion B of the system shown in FIG. 6.
Figure 8:
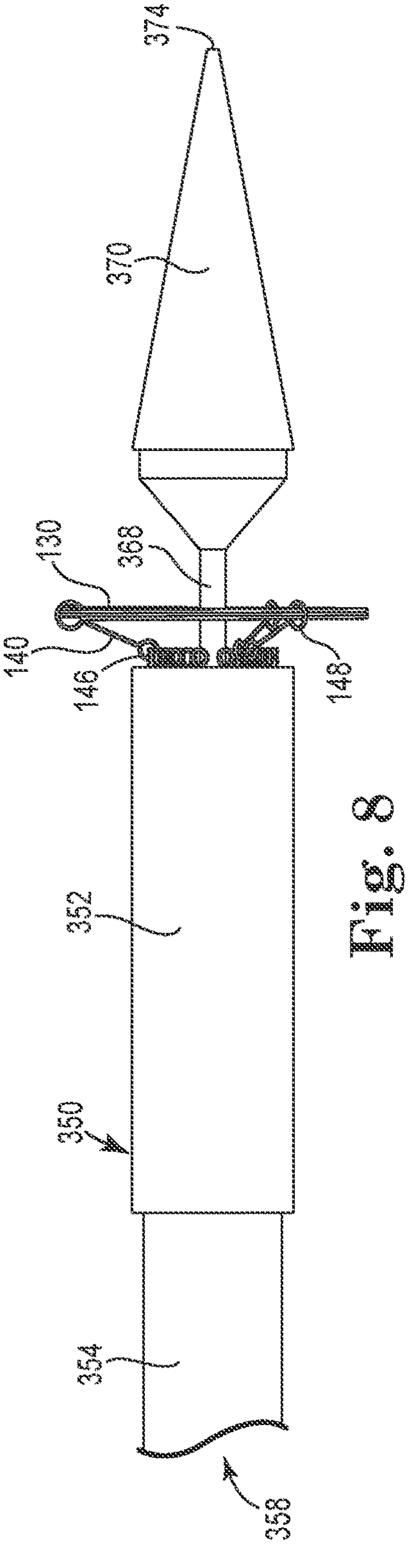
FIG. 8 illustrates a side view of distal end portion B of the system shown in FIG. 6.

FIGS. 7 and 8 illustrate a distal end portion (indicated as B) of system 300, at the stage of deployment as in FIG. 6. FIG. 7 illustrates a perspective view of distal end B and FIG. 8 illustrates a side view of distal end B.

Figures 9, 10, 11:
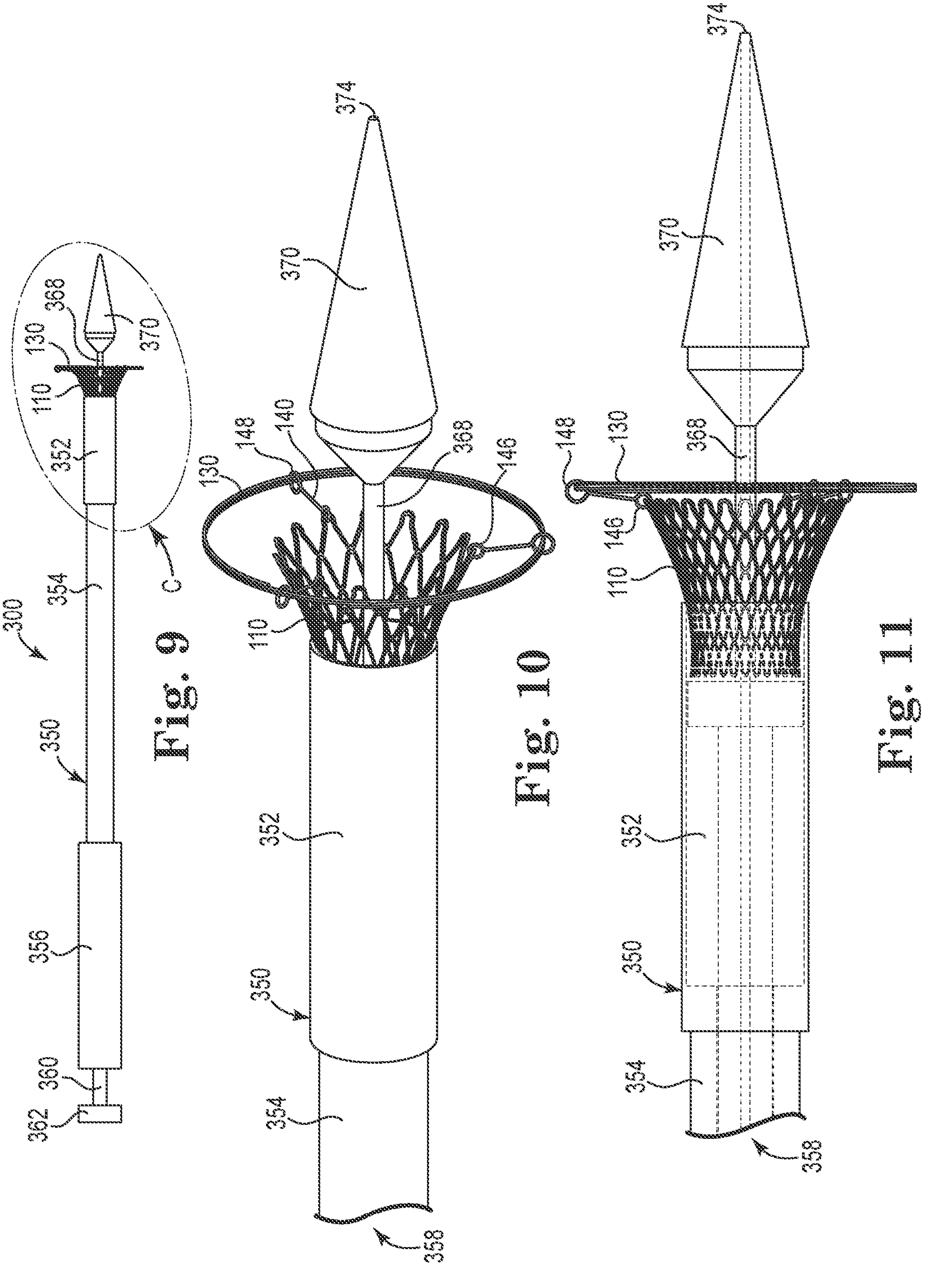
FIG. 9 illustrates a side view of the system of FIGS. 3 and 6 at a later stage in delivery of the prosthetic heart valve of the system.
FIG. 10 illustrates a perspective view of distal end portion C of the system shown in FIG. 9.
FIG. 11 illustrates a side view of distal end portion C of the system shown in FIG. 9, with interior shown in shadow.

FIG. 9 illustrates the system 300 after the pushing rod has been pushed even further distally than in FIG. 6. As shown, the expandable stent portion 110 has partially exited the distal end 359 of the sheath 350.

FIGS. 10 and 11 illustrate a distal end portion (indicated as C) of system 300, at the stage of deployment as in FIG. 9. FIG. 10 illustrates a perspective view of distal end C and FIG. 11 illustrates a side view of distal end C. FIG. 11 also shows, in shadow, the remainder of the prosthetic heart valve 100 that has not yet exited the sheath 350, as well as the pushing rod 360.

At this point in the delivery of the prosthetic heart valve 100, it is preferred for the surgeon (or operator) to pull the whole system 300, including the prosthetic heart valve 100, back proximally. The proximal pull preferably enables the spring 130 to engage into the proper implantation position. For the mitral valve, for example, the system 300 is pulled back once the device 100 has partially exited sheath 350, with sheath 350 being in the vicinity of the mitral valve annulus. Preferably, in the mitral valve application, the spring 130 is seated in the left atrium adjacent the atrial side of the mitral valve annulus. Depending upon the desired location and purpose for the prosthetic heart valve, however, adjustments may be made in order to allow for proper placement of the prosthetic heart valve.

Although the embodiment of the inventive system shown and described herein may not allow the prosthetic heart valve 100 to be retracted back into the sheath 350 for possible re-positioning, it is contemplated that other embodiments of inventive systems may have such an ability. For example, the prosthetic heart valve may be configured such that the expandable stent, support arms and spring may be retracted back into the sheath after being either partially deployed or completely deployed. Retractability may be desired, for example, if during deployment the surgeon (or operator) recognizes by image guidance means that the prosthetic heart valve is not being deployed in a proper place.

Figure 12:
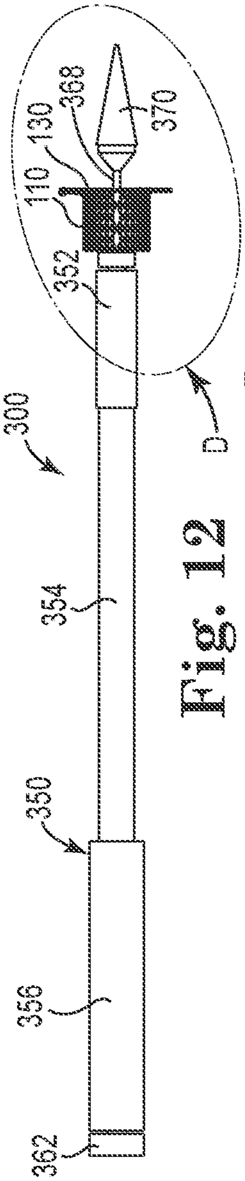
FIG. 12 illustrates a side view of the system of FIGS. 3, 6 and 9 at a later stage in delivery of the prosthetic heart valve of the system.

FIG. 12 illustrates the system 300 once the pushing rod 360 has been pushed even further distally from the stage of deployment shown in FIG. 9. Prosthetic heart valve 100 is no longer enclosed in the sheath 350, and is fully deployed.

Figure 13:
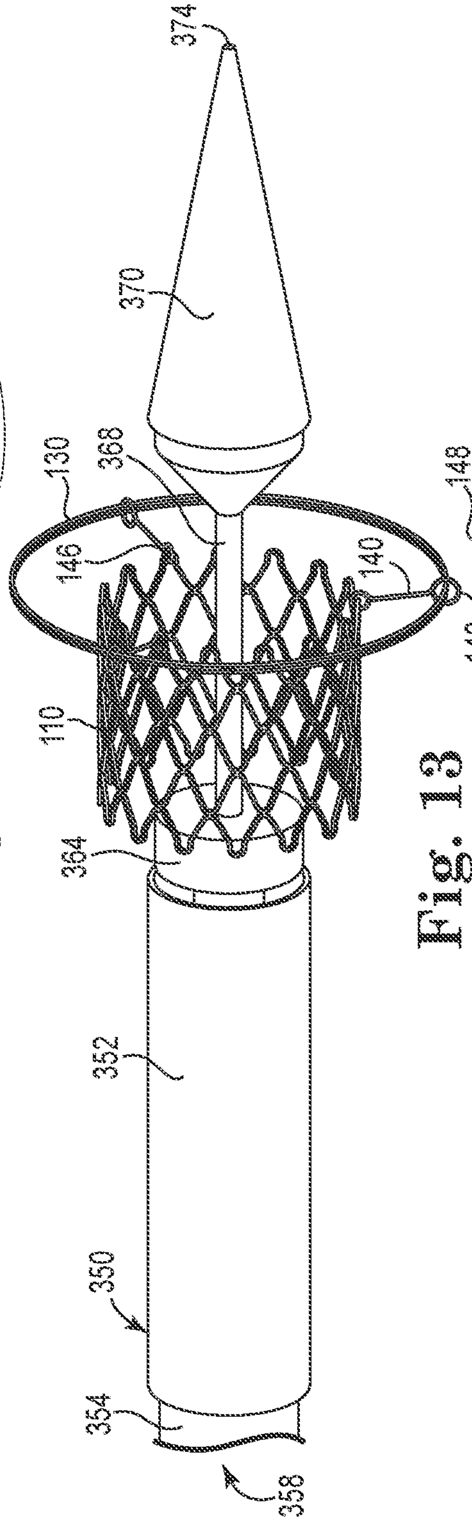
FIG. 13 illustrates a perspective view of distal end portion D of the system shown in FIG. 12.
Figure 14:
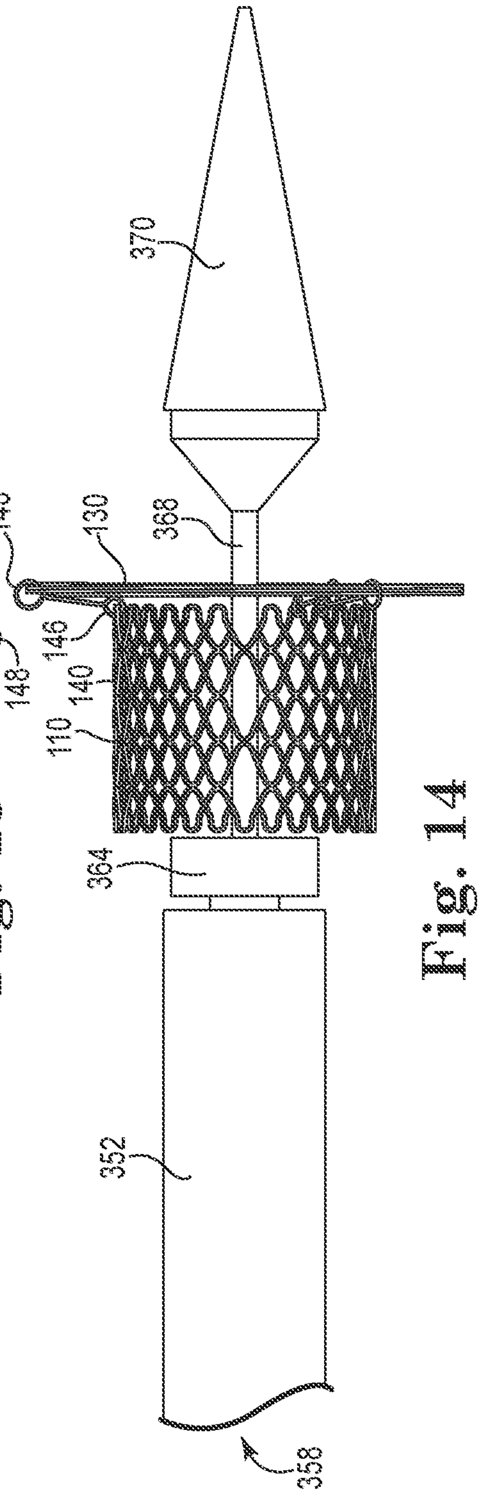
FIG. 14 illustrates a side view of distal end portion D of the system shown in FIG. 12.

FIGS. 13 and 14 illustrate a distal end portion (indicated as D) of system 300, at the stage of deployment as in FIG. 12. FIG. 13 illustrates a perspective view of distal end D and FIG. 14 illustrates a side view of distal end D.

Figure 15:
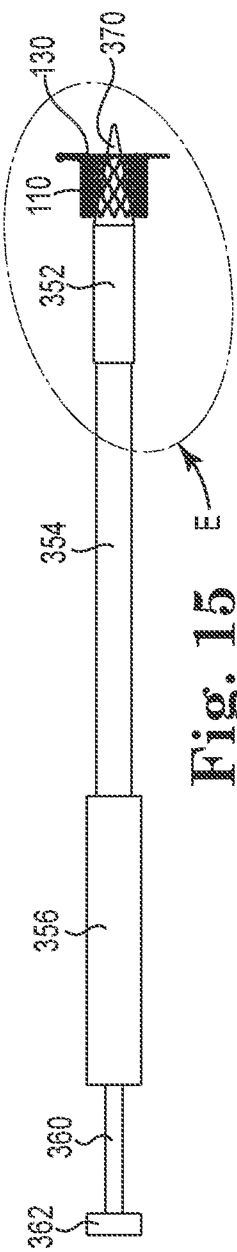
FIG. 15 illustrates a side view of the system of FIGS. 3, 6, 9, and 12 at a later stage in delivery of the prosthetic heart valve of the system.

FIG. 15 illustrates the system 300 once the prosthetic heart valve 100 has been fully deployed. The pushing rod 360 has been pulled proximally in order to pull the dilator 370 back in contact with the sheath 350. Next, the sheath 350, pushing rod 360 and dilator 370 will be retracted and removed from the body, leaving the prosthetic heart valve 100 behind.

Figure 16:
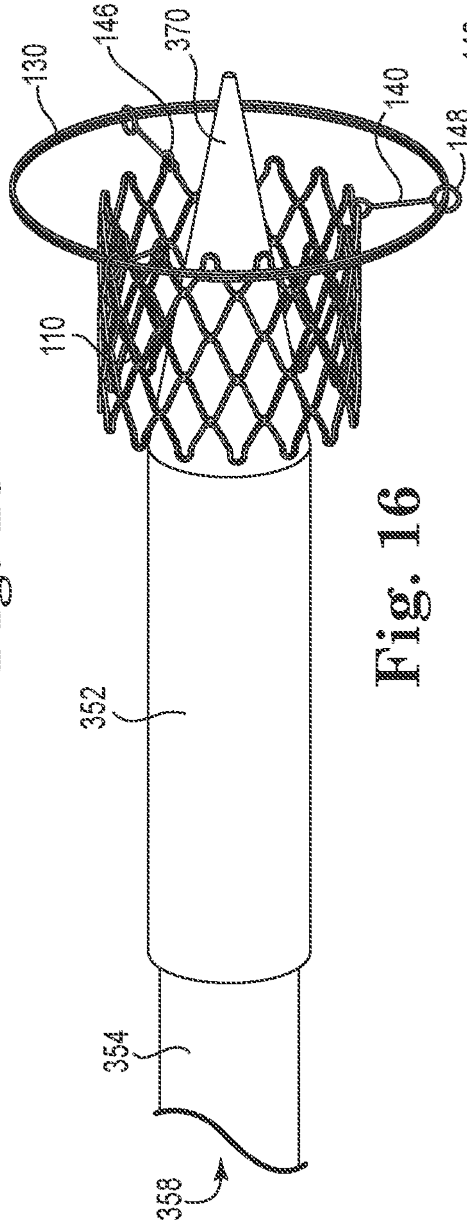
FIG. 16 illustrates a perspective view of distal end portion E of the system shown in FIG. 15.
Figure 17:
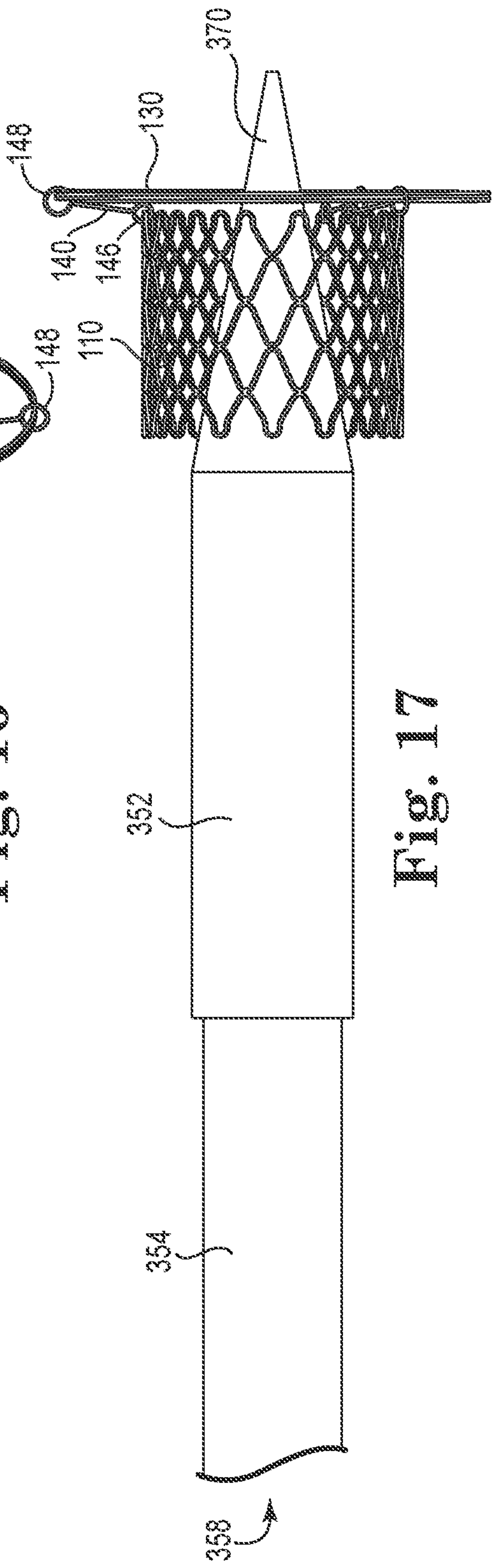
FIG. 17 illustrates a side view of distal end portion E of the system shown in FIG. 15.

FIGS. 16 and 17 illustrate a distal end portion (indicated as E) of system 300, at the stage of deployment as in FIG. 15. FIG. 16 illustrates a perspective view of distal end E and FIG. 17 illustrates a side view of distal end E.

Figure 19:
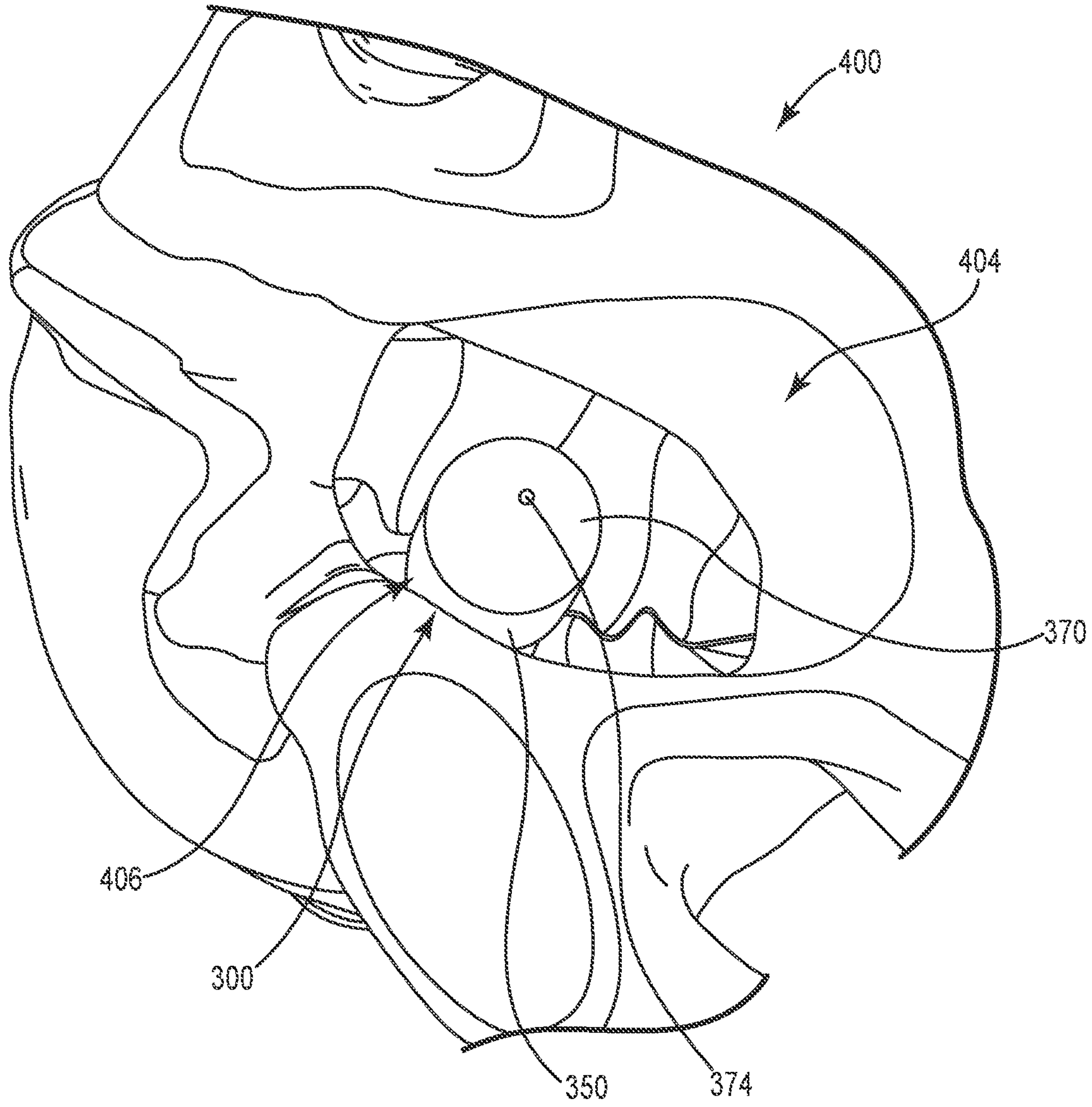
FIG. 19 schematically illustrates a top view of a heart with left atrium partially cut-away in order to view the inventive system being inserted through a mitral valve annulus.
Figure 20:
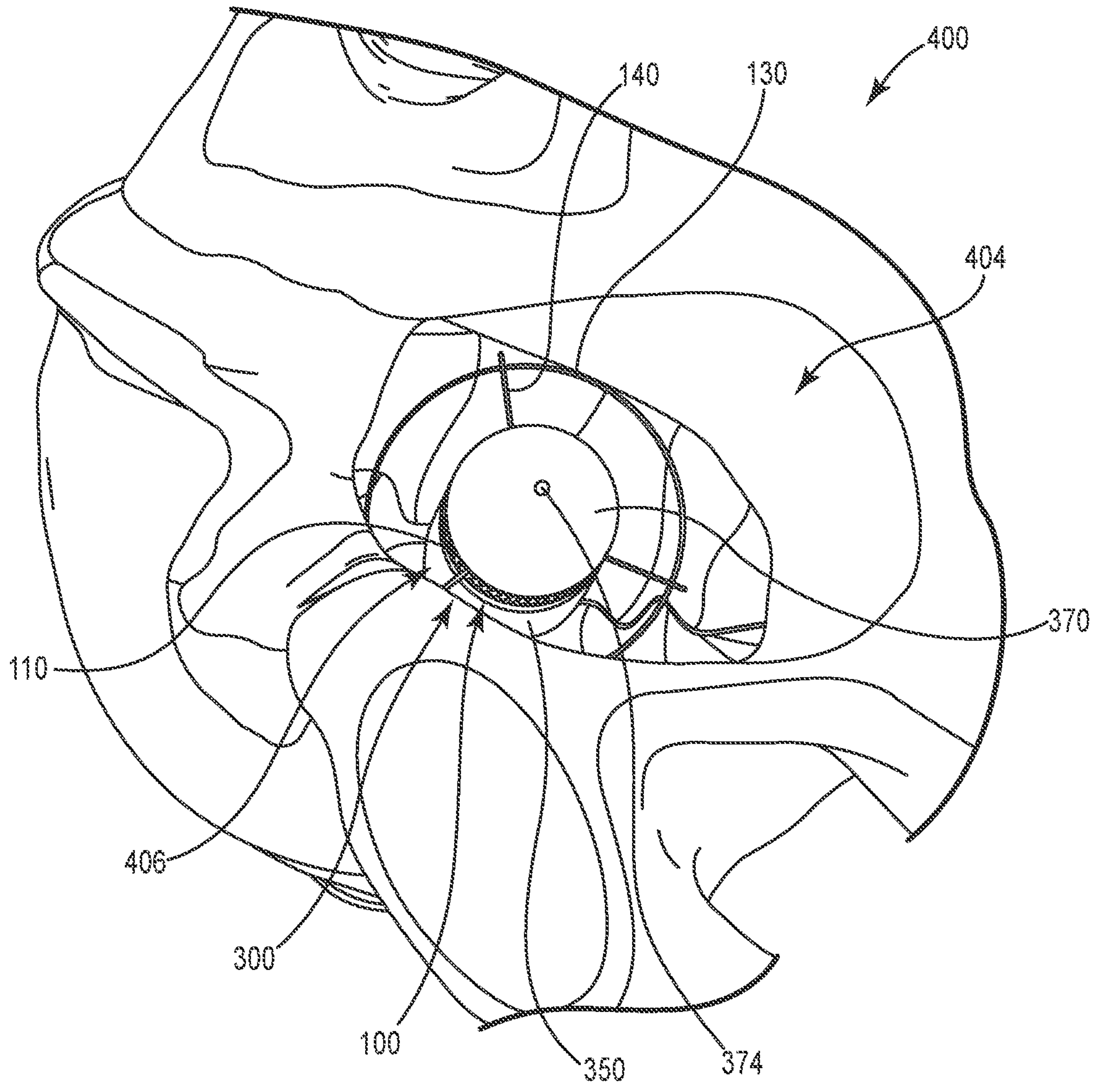
FIG. 20 is the heart and system shown in FIG. 19 with the prosthetic valve device of the system being partially deployed.

FIGS. 19 and 20 are schematic representations of a heart 400 with a view from above and including a view into a left atrium 404 (some of left atrium is cut-away in figure). FIG. 19 shows the inventive system 300 inserted through the mitral valve annulus 406, with its distal end, including dilator 370 (with opening 374) and sheath 350, extending into the left atrium 404. FIG. 20 shows the inventive prosthetic valve 100 partially deployed, with the amount of deployment being approximately as in the system 300 shown in FIGS. 6-8. As shown, expandable stent portion 110 has partially exited or been partially deployed from the distal end of sheath 350. Three support arms 140 are extended and spring 130 is released or deployed, and is being held through loops (not visible) on ends of the support arms 140.

In an alternative embodiment of the system of the invention, it may be desired to includes means for keeping the expandable stent portion inside a retractable sheath and compressed until the retractable sheath has been retracted enough to fully clear the expandable stent portion. Therefore, the expandable stent portion would not be in a partially deployed configuration as in earlier figures. This alterative embodiment may be desired because it is possible that stored energy in a compressed end of the prosthetic heart valve may force the expandable stent portion out of a distal end of a sheath prematurely and before the expandable stent portion is desired to be fully deployed. Such premature release of the prosthetic heart valve could result in improper placement of the device, for example. In order to avoid such premature release upon deployment, the invention contemplates using means to prevent such premature release.

Figure 23:
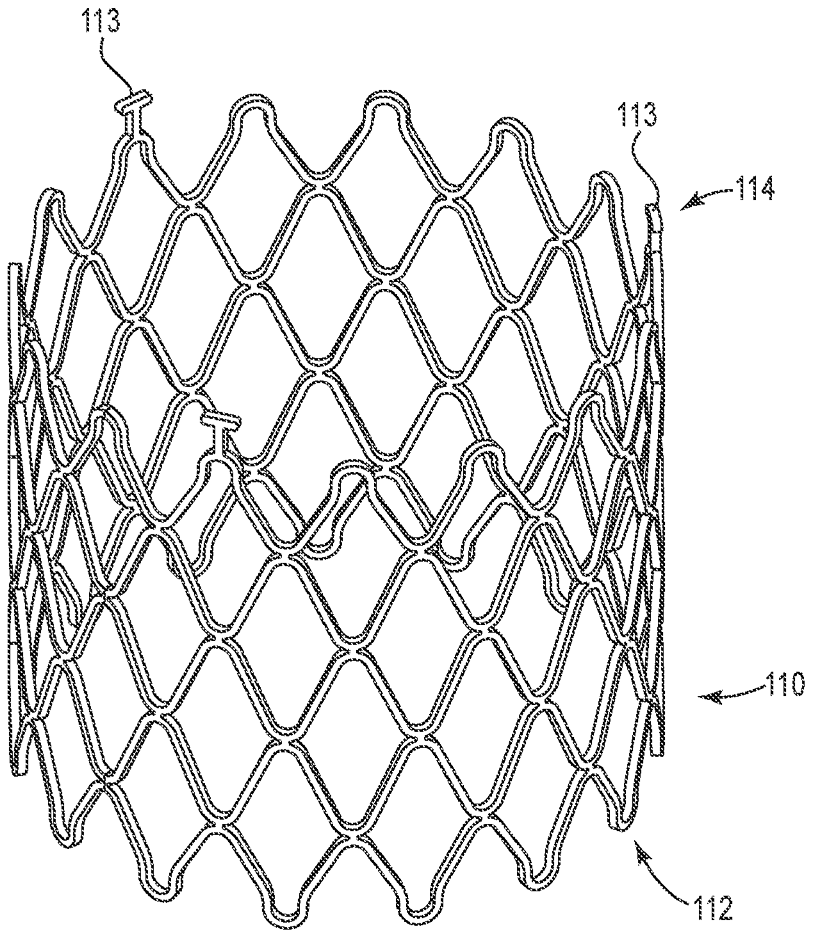
FIG. 23 illustrates a perspective view of an expandable stent portion of an embodiment of a prosthetic valve, in accordance with the invention.
Figure 24:
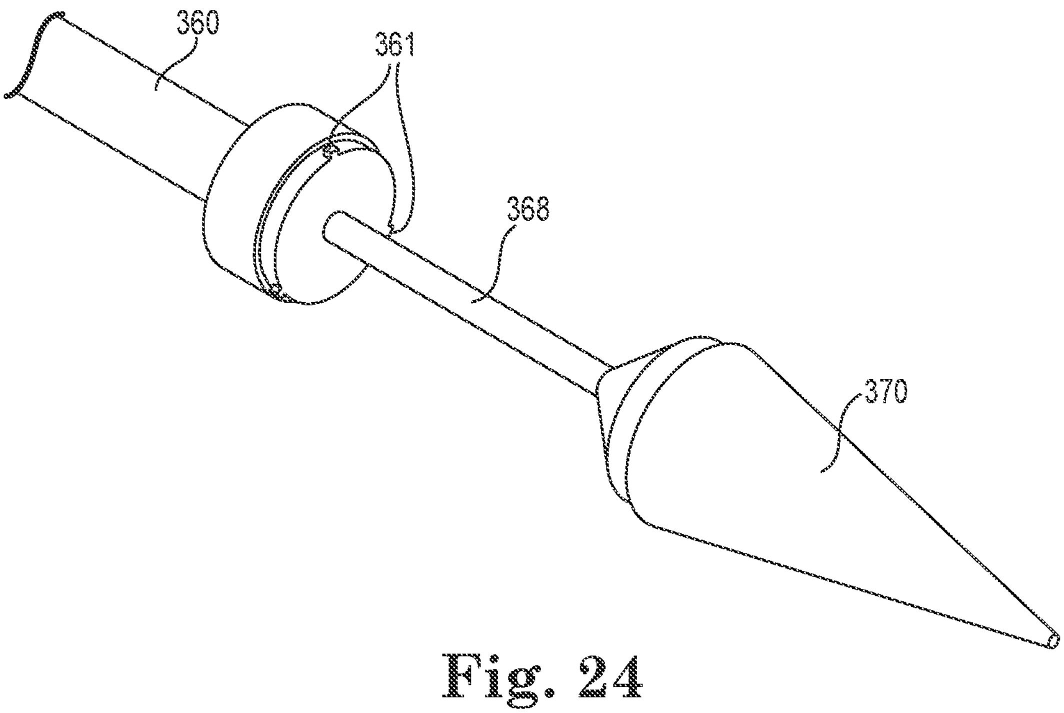
FIG. 24 illustrates a perspective view of a distal end portion of an embodiment of a system, in accordance with the invention.

FIGS. 23 and 24 show illustrative means for preventing premature release of the device from a delivery system. For example, in FIG. 23, retainers 113 are added to the second end 114 of the expandable stent portion 110 that prevent the expandable stent portion 110 from exiting the sheath 350 until the expandable stent portion 110 has fully cleared the sheath 350. The retainers 113 would mate, for example, with some portion of the pushing rod 360. In FIG. 24, another alternative means for preventing premature release of the device from the delivery system 300 is shown as bosses 361 located on the pushing rod 360. the prosthetic heart valve would be enclosed in a retractable sheath (not shown) and surrounding extension 368 of pushing rod 360. The bosses 361 would hold a proximal end of a collapsed prosthetic heart device between the retractable sheath and pushing rod 360 until a proximal end of an expandable sheath portion of the prosthetic heart valve fully cleared the retractable sheath. The bosses 361 and retainers 113 are examples of means for preventing premature release, however, and other means are also contemplated.

All publications, patents and patent documents cited are fully incorporated by reference herein, as though individually incorporated by reference. Numerous characteristics and advantages of the invention meant to be described by this document have been set forth in the foregoing description. It is to be understood, however, that while particular forms or embodiments of the invention have been illustrated, various modifications, including modifications to shape, and arrangement of parts, and the like, can be made without departing from the spirit and scope of the invention.

What is claimed is:

1. A prosthetic valve, comprising:
- a first expandable annular member defining an inner lumen, and having a longitudinal axis;
- a valvular element disposed in the inner lumen of the first expandable annular member;
- a second expandable annular member having a circumference greater than a circumference of the first expandable annular member when the prosthetic valve is in an expanded configuration; and
- a connecting element connecting the first expandable annular member to the second expandable annular member, the connecting element being a separate element from each of the first and second expandable annular members, the connecting element having a loop or eyelet for connecting with the first expandable annular member, the connecting element configured to allow movement between the first and second expandable annular members such that the connecting element is configured to laterally rotate outward from the first expandable annular member during expansion of the second expandable annular member wherein at least a portion of the connecting element is capable of extending generally perpendicular to the longitudinal axis of the first expandable annular member when the second expandable annular member is in an expanded configuration, and wherein the second expanded annular member is configured to assist in the proper placement of the prosthetic valve within a body.

2. The prosthetic valve of claim 1, wherein the second expandable annular member comprises a wire that forms an expandable circular loop.

3. The prosthetic valve of claim 2, wherein the wire comprises a shape memory alloy.

4. The prosthetic valve of claim 2, wherein the wire forms a torsion spring.

5. The prosthetic valve of claim 1, wherein the valvular element comprises at least one leaflet.

6. The prosthetic valve of claim 1, wherein the prosthetic valve is a prosthetic heart valve.

7. The prosthetic valve of claim 6, wherein the prosthetic heart valve is a prosthetic mitral valve.

8. The prosthetic valve of claim 6, wherein the prosthetic heart valve is a prosthetic aortic valve.

9. The prosthetic valve of claim 1, wherein the second expandable annular member comprises a radiopaque material.

10. The prosthetic valve of claim 1, wherein the connecting element has a second loop or eyelet for connecting with the second expandable annular member.

11. A method of implanting a prosthetic valve, comprising:
- inserting a delivery system with a prosthetic valve into a body lumen, the prosthetic valve comprising
  - a first expandable annular member having an inner lumen, and a longitudinal axis,
  - a valvular element disposed in the inner lumen of the first expandable annular member, and
  - a second expandable annular member connected by a connecting element to the first expandable annular member, the connecting element being a separate element from each of the first and second expandable annular members, the connecting element having a loop or eyelet for connecting with the first expandable annular member, wherein the circumference of the second expandable annular member is greater than a circumference of the first expandable annular member when the prosthetic valve is in an expanded configuration;
- at least partially deploying the prosthetic valve at an implantation location such that the connecting element pivots outwardly relative to the first expandable annular member to permit expansion of the second expandable annular member, wherein at least a portion of the connecting element is capable of extending generally perpendicular to the longitudinal axis of the first expandable annular member when the second expandable annular member is in an expanded configuration; and
- proximally pulling the prosthetic valve to engage at least a portion of the second expandable annular member with a wall of the body lumen.

12. The method of claim 11, wherein the step of inserting the delivery system into the body lumen comprises transapically inserting the delivery system into a heart.

13. The method of claim 11, wherein the step of proximally pulling the prosthetic valve engages at least a portion of the second expandable annular member with a heart wall in a left atrium adjacent a mitral valve annulus.

14. The method of claim 11, wherein the second expandable annular member comprises a wire.

15. The method of claim 11, wherein the second expandable annular member comprises a radiopaque material.

16. The method of claim 11, wherein the step of at least partially deploying the prosthetic valve includes viewing the prosthetic valve using image guidance.

17. The method of claim 16, wherein the image guidance may be selected from the group consisting of fluoroscopy, ultrasonic means, magnetic resonance, X-ray, and computer tomography.

18. The method of claim 11, wherein the connecting element has a second loop or eyelet for connecting with the second expandable annular member.

19. A method of implanting a prosthetic valve, comprising:

inserting a delivery system with a prosthetic valve into a body lumen, the prosthetic valve comprising a first expandable annular portion having an inner lumen, and a longitudinal axis, a valvular element disposed in the inner lumen of the first expandable annular portion, and a second expandable annular portion rotatably connected to the first expandable annular portion by a connecting element, the connecting element being a separate element from each of the first and second expandable annular portions, the connecting element having a loop or eyelet for connecting with the first expandable annular portion, wherein the circumference of the second expandable annular portion is greater than a circumference of the first expandable annular portion when the prosthetic valve is in an expanded configuration;

at least partially deploying the prosthetic valve at an implantation location such that the connecting element rotates outwardly relative to the first expandable annular portion to permit expansion of the second expandable annular portion, wherein at least a portion of the connecting element is capable of extending generally perpendicular to the longitudinal axis of the first expandable annular portion when the second expandable annular member is in the expanded configuration; and proximally pulling the prosthetic valve to engage at least a portion of the second expandable annular portion with a heart wall in a left atrium adjacent a mitral valve annulus.

20. The method of claim 19, wherein the second expandable annular portion comprises a wire.

* * * * *